(12) United States Patent
Subbian

(10) Patent No.: US 10,570,424 B2
(45) Date of Patent: Feb. 25, 2020

(54) RECOMBINANT METHANOTROPHIC BACTERIUM AND A METHOD OF PRODUCTION OF SUCCINIC ACID FROM METHANE OR BIOGAS THEREOF

(71) Applicant: STRING BIO PRIVATE LIMITED, Malleswaram, Bangalore (IN)

(72) Inventor: Ezhilkani Subbian, Bangalore (IN)

(73) Assignee: STRING BIO PRIVATE LIMITED, Malleswaram, Bangalore (IN)

( * ) Notice: Subject to any disclaimer, the term of this patent is extended or adjusted under 35 U.S.C. 154(b) by 222 days.

(21) Appl. No.: 15/303,184

(22) PCT Filed: Apr. 13, 2015

(86) PCT No.: PCT/IN2015/000169
§ 371 (c)(1),
(2) Date: Oct. 10, 2016

(87) PCT Pub. No.: WO2015/155791
PCT Pub. Date: Oct. 15, 2015

(65) Prior Publication Data
US 2017/0121740 A1 May 4, 2017

(30) Foreign Application Priority Data

Apr. 11, 2014 (IN) .......................... 1910/CHE/2014

(51) Int. Cl.
| | |
|---|---|
| *C12P 7/46* | (2006.01) |
| *C12N 9/04* | (2006.01) |
| *C12N 9/88* | (2006.01) |
| *C12N 9/00* | (2006.01) |
| *C12N 15/52* | (2006.01) |
| *C12N 15/74* | (2006.01) |

(52) U.S. Cl.
CPC .............. *C12P 7/46* (2013.01); *C12N 9/0006* (2013.01); *C12N 9/88* (2013.01); *C12N 9/93* (2013.01); *C12N 15/52* (2013.01); *C12N 15/74* (2013.01); *C12Y 101/01037* (2013.01); *C12Y 401/01031* (2013.01); *C12Y 604/01001* (2013.01); *Y02E 50/343* (2013.01)

(58) Field of Classification Search
CPC ........... C12P 7/46; C12N 15/74; C12N 15/52; C12N 9/88; C12N 9/93; C12N 9/0006; C12Y 604/01001; C12Y 101/01037; C12Y 401/01031; Y02E 50/343
See application file for complete search history.

(56) References Cited

U.S. PATENT DOCUMENTS

| | | |
|---|---|---|
| 2003/0003528 A1 | 1/2003 | Brzostowicz et al. |
| 2003/0032141 A1 | 2/2003 | Nguyen et al. |
| 2009/0070897 A1 | 3/2009 | Goldman et al. |
| 2013/0260433 A1 | 10/2013 | Zhang |

FOREIGN PATENT DOCUMENTS

| | | | |
|---|---|---|---|
| WO | WO 2013/003432 | * | 1/2013 |
| WO | WO 2013/003744 A2 | | 1/2013 |
| WO | WO 2013/142033 | * | 9/2013 |

OTHER PUBLICATIONS

Chistoserdova et al., Journal of Bacteriology 185(10):2980-2987, 2003.*
Riley et al., GenBank accession No. NP_418439, Jan. 11, 2012.*
Riley et al., GenBank accession No. NP_417703, Jan. 11, 2012.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M. Gene 234:187-208, 1999.*
International Search Report issued in PCT/IN15/00169 dated Jan. 19, 2016.

\* cited by examiner

*Primary Examiner* — Delia M Ramirez
(74) *Attorney, Agent, or Firm* — Foley & Lardner LLP

(57) ABSTRACT

The present disclosure provides for production of succinic acid from organic waste or biogas or methane using recombinant methanotrophic bacterium. In one embodiment, the recombinant methanotrophic bacterium includes exogenous nucleic acid(s) or gene(s) encoding for specified enzymes. In a further embodiment, succinic acid producing capacity of the recombinant methanotrophic bacterium is increased above the basal level by overexpression or/and downregulation of selected gene(s). In another embodiment, a process of producing succinic acid using the recombinant methanotrophic bacterium is disclosed. The present invention successfully solves the problems in converting organic waste to a useful chemical thereby providing an environment-friendly and commercially viable solution for waste management.

10 Claims, 7 Drawing Sheets
Specification includes a Sequence Listing.

SEQUENCE LISTING

<160> NUMBER OF SEQ ID NOS: 34

<210> SEQ ID NO 1

```
<211> LENGTH: 939
<212> TYPE: DNA
<213> ORGANISM: Escherichia coli
<220> FEATURE:
<223> OTHER INFORMATION: Malate dehydrogenase

<400> SEQUENCE: 1
atgaaagtcg cagtcctcgg cgctgctggc ggtattggcc aggcgcttgc actactgtta      60
aaaacccaac tgccttcagg ttcagaactc tctctgtatg atatcgctcc agtgactccc     120
ggtgtggctg tcgatctgag ccatatccct actgctgtga aaatcaaagg tttttctggt     180
gaagatgcga ctccggcgct ggaaggcgca gatgtcgttc ttatctctgc aggcgtagcg     240
cgtaaaccgg gtatggatcg ttccgacctg tttaacgtta acgccggcat cgtgaaaaac     300
ctggtacagc aagttgcgaa aacctgcccg aaagcgtgca ttggtattat cactaacccg     360
gttaacacca cagttgcaat tgctgctgaa gtgctgaaaa agccggtgt ttatgacaaa      420
acaaactgt tcggcgttac cacgctggat atcattcgtt ccaacacctt tgttgcggaa     480
ctgaaaggca acagccagg cgaagttgaa gtgccggtta ttggcggtca ctctggtgtt      540
accattctgc cgctgctgtc acaggttcct ggcgttagtt ttaccgagca ggaagtggct     600
gatctgacca aacgcatcca gaacgcgggt actgaagtgg ttgaagcgaa ggccggtggc     660
gggtctgcaa ccctgtctat gggccaggca gctgcacgtt ttggtctgtc tctggttcgt     720
gcactgcagg gcgaacaagg cgttgtcgaa tgtgcctacg ttgaaggcga cggtcagtac     780
gcccgttcct ctctctcaacc gctgctgctg ggtaaaaacg cgtggaaga gcgtaaatct     840
atcggtaccc tgagcgcatt tgaacagaac gcgctggaag gtatgctgga tacgctgaag     900
aaagatatcg ccctgggcga agagttcgtt aataagtaa                            939

<210> SEQ ID NO 2
<211> LENGTH: 3291
<212> TYPE: DNA
<213> ORGANISM: Pseudomonas aeruginosa
<220> FEATURE:
<223> OTHER INFORMATION: Pyruvate Carboxylase

<400> SEQUENCE: 2
gtgaccgctc ccccttcaa cgccttgctg atcgccaacc gcggcgagat cgccattcgc       60
atcgcccgcg cctgcgccga cctgggtatc cgctcggtgg cggtgttcgc ggaagacgat     120
gccgcgtccc tgcacgtgcg gaaggccgat gtcgcgctgc cgctggccgg ccgtggcgtg     180
gcggcctatc tcgacatgga tcggctggtc gcgctggccc tggagcaggg ctgcgaggcg     240
atccatccgg gctacggttt cctcgccgag aacggcgaat cgcccggcg ctgccagcgc     300
gcgggcatcc acttcgtcgg gccgcaagcg gaagtgctcg acctgctcgg cgacaaggct     360
gccgcgcgcg ccctggccga gcgcctggag gtgccgctgg tggccgggat caaccgtgcg     420
gtcagcgtcg aagaggccga ggcgttcctg gaagggctgg gcgatggcgc gcgcgtgatg     480
ctcaaggccc ttgccggcgg cggcgacgt ggcatgcgcg cggtggagga ggttgcgcaa      540
ctggccgatg cctaccgccg ctgccgtgcc gaggcgcagg cggcgttcgg ccgggacgag     600
ttatacgtcg agcaacgggt agcgcgggcg cggcacatcg aggtgcaggt gctcggcgac     660
ggcagcggtg cggtcagcca cctctgggag cgcgattgca gcctgcaacg cgccagcag      720
aagctgctgg agatcgcgcc cagcccggac ctgccggagg ccactcgcga ggcgctgatc     780
gattgcgccc tgcgcatggc cggcgcggtg cgctatcggg ggatcggtac cttcgagttc     840
ctggtcgacg aggagcgccc cggggcactc tatttcatgg aagccaatcc gcgtatccag     900
```

```
gtggagcaca ccgtcaccga ggaagtcacc ggggtcgacc tgctgcacgc ccagttgcgt      960
ctcgccgccg gcatggagct tgccgccctc ggcctggagc gaccgccggc gatcggcggc     1020
tgcgcggtgc aactgcggat caacctggag accctggcgg tcgacggcag cgcccgtccg     1080
gcggtgggca ctatcggcgc ctacgaaccg cccagcggtc ccggcctgcg ggtggacggc     1140
tacggctatg ccggctatcg ggtcagcccc agctacgatt cgctgctggc caagctggtc     1200
gtgcgcggcg cggattatcc cgccgcgttg cgccgggcct accgggcgct ctgcgaattc     1260
cgcctggagg gcgtggcgag caacctggac ctgctgcgca accttctgct gcatccggcg     1320
gtacaggcca accgggtcga cacccgcttc gtcgaaagcc acctggagac actgctggcg     1380
cctatcccgg cgagccatcc gcggctccgc gccgagtgcc cgctcgccga ggacgccgcg     1440
cctgcgcggg tcgaggcgcc actcggcagc ctgccgctgt cggcgccgag cagcggggtg     1500
ctggtggccc tggaagtggc cgagggcgaa cgggtgcgtg ccggccagcg ggtcgcgatc     1560
ctggaagcga tgaagatgga gttcgaggtc aaggcacccg gcgggggat cgtccggcgg      1620 ctcgcggcga gcctcgggga gcctctggag gagggcgcga cgctgctgtt ccttgaaccg     1680
acggaggatg acgacgagca ggcaccgacc gaacaggcgc tggacctggc gcatatccgc     1740
gccgatctcg ccgaggtact cgagcgccag gcagcgctgg gcgacgagcg tcgtccgcag     1800
gcgcttgcca gcggcgcaa gaccggacag cgtaccgcgc gggagaacgt gctcgacctg      1860
ctggacgagg gcagcttcag cgaatatggc ggtttcgccc tggccgccca cgtcgccgg     1920 cgttccgccg aggagttgct ggagctgagc cccgccgatg gcctggtcgc cggcaccggt     1980
acggtggggg ccgccagctt cggcgtgcag gccgcgcgtt gcctggtact ggcctacgac    2040
tacacggtgt tcgccggcac ccagggggtg atgaaccaca agaagaccga ccgcctgctc    2100
ggcctggccg aacagtggcg cttgccgctg gtgctgttcg ccgagggcgg cggcgggcgc    2160
ccgggcgata ccgatttcgt cggcgtcgcc ggcctcgatt gccataccct cgtcggcatg    2220
gcccggctct ccgggctggt gccgctggtg ggagtggtct ccggtcgctg cttcgccggc    2280
aatgccgcgt tgctgggctg ctgcgatgtg atcatcgcca cccgcgacgc caccatcggc    2340
atggccggcc cggcgatgat cgagggcggc ggcctgggcc gtttcgccgc cgaggaggtc    2400
ggtccgacgg gcgtgcaggg gcccaacgga gtgatcgacg tactggtgga ggacgaggcc    2460
gaagcggtcg cggtggccag cgcgtatctc ggctatttcc agggcccgct gcccgactgg    2520
agttgcgccg accagcgcga gttgcgccac ctggtgccgg agaaccgcct gcgtgcctac    2580
gacatccgcc aggcgatcga ggtcctggcc gaccggggca cgtgctgga actgcggcgc     2640 cagttcgctc ccggcctggt caccgcgctg ctgcgcatcg agggccgggc gttcggcctg    2700
atcgccaaca accctggcca tctcggcggc gccatcgatg ccgcggctgg cgacaaggcc    2760
gcgcgcttca tgcagttgtg cgacgccttc gacatcccga tcgtctcgct ctgcgacacc    2820
cctggcttca tggtcggccc ggaggcgaa aaacaggcca cggtgcgcca cgtctcgcgg     2880
atgttcgtca gcgccgccag cctgacggtg ccgttcttca ccgtggtcct gcgcaagggc    2940
tacggactgg gagcccaggc catggcggcg ggcagcttcc attcgccgct gttcaccgtc    3000
gcctggccca gcgcgagtt cggcgccatg ggcctggaag gcgcggtgcg gctgggcttc     3060
gccaaggagc tggcggccga ggaagatccc cagcggcgcg aggcgctgtt ccgcggcatg    3120
gtggacaagg cctaccgcaa cggcaaggcg ctgaacatgg ccagctacct ggagatcgac    3180
gcggtgatcg acccggcgga gacccgcgcc tggctcctgc gcggcctggc cgtcgccgga    3240
```

```
                                                    -continued gaaccggtgc gagggcggg gcgcaagcgg ccgttcgtgg atacctggta g           3291

<210> SEQ ID NO 3
<211> LENGTH: 2652
<212> TYPE: DNA
<213> ORGANISM: Escherichia coli
<220> FEATURE:
<223> OTHER INFORMATION: Phosphoenol pyruvate carboxylase

<400> SEQUENCE: 3
atgaacgaac aatattccgc attgcgtagt aatgtcagta tgctcggcaa agtgctggga     60 gaaccatca aggatgcgtt gggagaacac attcttgaac gcgtagaaac tatccgtaag    120
ttgtcgaaat cttcacgcgc tggcaatgat gctaaccgcc aggagttgct caccaccta    180 caaaatttgt cgaacgacga gctgctgccc gttgcgcgtg cgtttagtca gttcctgaac    240
ctggccaaca ccgccgagca ataccacagc atttcgccga aaggcgaagc tgccagcaac    300
ccggaagtga tcgcccgcac cctgcgtaaa ctgaaaaacc agccggaact gagcgaagac    360
accatcaaaa aagcagtgga atcgctgtcg ctggaactgg tcctcacggc tcacccaacc    420
gaaattaccc gtcgtacact gatccacaaa atggtggaag tgaacgcctg tttaaaacag    480
ctcgataaca aagatatcgc tgactacgaa cacaaccagc tgatgcgtcg cctgcgccag    540
ttgatcgccc agtcatggca taccgatgaa atccgtaagc tgcgtccaag cccggtagat    600
gaagccaaat ggggctttgc cgtagtgaa acagcctgt ggcaaggcgt accaaattac    660
ctgcgcgaac tgaacgaaca actggaagag aacctcggct acaaactgcc cgtcgaattt    720
gttccggtcc gttttacttc gtggatgggc ggcgaccgcg acggcaaccc gaacgtcact    780
gccgatatca cccgccacgt cctgctactc agccgctgga aagccaccga tttgttcctg    840
aaagatattc aggtgctggt ttctgaactg tcgatggttg aagcgacccc tgaactgctg    900
gcgctggttg cgaagaagg tgccgcagaa ccgtatcgct atctgatgaa aaacctgcgt    960
tctcgcctga tggcgacaca ggcatggctg gaagcgcgcc tgaaaggcga agaactgcca   1020
aaaccagaag gcctgctgac acaaaacgaa gaactgtggg aaccgctcta cgcttgctac   1080
cagtcacttc aggcgtgtgg catgggtatt atcgccaacg cgatctgct cgacaccctg   1140 cgccgcgtga atgtttcgg cgtaccgctg gtccgtattg atatccgtca ggagagcacg   1200
cgtcataccg aagcgctggg cgagctgacc cgctacctcg gtatcggcga ctacgaaagc   1260
tggtcagagg ccgacaaaca ggcgttcctg atccgcgaac tgaactccaa acgtccgctt   1320
ctgccgcgca actggcaacc aagcgccgaa acgcgcgaaa tgctcgatac ctgccaggtg   1380
attgccgaag caccgcaagg ctccattgcc gcctacgtga tctcgatggc gaaaacgccg   1440
tccgacgtac tggctgtcca cctgctgctg aaagaagcgg gtatcgggtt tgcgatgccg   1500
gttgctccgc tgtttgaaac cctcgatgat ctgaacaacg ccaacgatgt catgacccag   1560
ctgctcaata ttgactggta tcgtggcctg attcagggca acagatggt gatgattggc   1620 tattccgact cagcaaaaga tgcgggagtg atggcagctt cctgggcgca atatcaggca   1680
caggatgcat taatcaaaac ctgcgaaaaa gcgggtattg agctgacgtt gttccacggt   1740
cgcggcggtt ccattggtcg cggcggcgca cctgctcatg cggcgctgct gtcacaaccg   1800
ccaggaagcc tgaaaggcgg cctgcgcgta accgaacagg gcgagatgat ccgctttaaa   1860
tatggtctgc cagaaatcac cgtcagcagc ctgtcgcttt ataccggggc gattctggaa   1920
gccaacctgc tgccaccgcc ggagccgaaa gagagctggc gtcgcattat ggatgaactg   1980
tcagtcatct cctgcgatgt ctaccgcggc tacgtacgtg aaaacaaaga ttttgtgcct   2040
```

```
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaagaagg ccaggaaccg    2580 gatcctcgcg tcgaacaagc gttaatggtc actattgccg ggattgcggc aggtatgcgt    2640
aataccggct aa                                                        2652

<210> SEQ ID NO 4
<211> LENGTH: 1263
<212> TYPE: DNA
<213> ORGANISM: Methylococcus capsulatus Bath
<220> FEATURE:
<223> OTHER INFORMATION: Phosphofructokinase

<400> SEQUENCE: 4
atggcggcgc ggaatgcttt ctatgcccag tccggcggtg tgaccgccgt tatcaatgca      60
tcggcctgcg gcgtgctgga gaccgccggg cagtatcccg accgtatcgg cacggttttac   120 gccgggcgta acggcatcgt cggtgcactg accgaggacc tgatcgatac cgggcaggag    180
agcgccgaag ccatcgccgc attgcgccac actccctccg gggcgttcgg ttcctgccgc    240
tacaagctca aagggctgga ggagaaccgg gcccagtacg aacggttgat cgaggtcttc    300
cgcgcccacg catcggcta tttcttctac aacggcggcg gggattccgc cgatacctgt    360
ctgaaagtct cccagctttc cgagaaattg ggttatccgt gcaggccgt ccatattccg    420 aagacggtgg acaacgacct gccgatcacc gactgctgtc cggggttcgg ttcggtcgcc    480
aagtacatag cggtatcggt acgcgaggcg agtttcgacg tacgctccat ggctgcgact    540
tccacctgca tcttcgtgct ggaagtcatg ggccgccacg cgggctggat cgccgccgcc    600
ggcggtctgg cgagtgacga gcggcatgag ctggctctgg tcatcttgtt tcccgaacag    660
gtgttcgacc cggaacggtt ctccggggcg gtggacgaaa aggtccggtc acatggctat    720
tgttcggtcg tggtgtcgga gggcattagg ggcgcggatg caggttcgt cgccgaatcc    780 ggcagccggg acgtgttcgg gcatgctcgg ctcggtgggg tggcgccggt catcgccgac    840
ctgatcaagg agcgcctggg ttacaaatac cactgggccg tcgccgatta cctgcagcgc    900
gcggcccggc acatcgcctc ccgcacggat gtcgagcagg cctatgcggt ggggaaggcg    960
ggcgtcgaga tggctctgaa agggctcagc gccgtgatgc cggccatcgt gcgcacctcg   1020
gattcgcctt accgttggga aatcacggcc gccagtctgg cggaggtggc caacgtcgaa   1080
aagaaaatgc ccctcgaatt catcagcgcc gacggtttcg gcatcaccga ggcctgccgc   1140
cggtacctcc ggcctctgat cgagggcgag gactaccctc cctatgccgg cggttttgccg   1200 gattatgtga cattgtgcaa tgtcgctgtc ccgaaaaaac tggccgcttc gttcagcgtc   1260
tga                                                                 1263

<210> SEQ ID NO 5
```

<211> LENGTH: 1467
<212> TYPE: DNA
<213> ORGANISM: Escherichia coli
<220> FEATURE:
<223> OTHER INFORMATION: Pyruvate Kinase

<400> SEQUENCE: 5

| | | | | | |
|---|---|---|---|---|---|
| atgacgaggg | gaattcgccg | taccaagatc | atcgccacgc | tggggccggc | ttccgagtct | 60 |
| ccggagatgc | tcgagagaat | cctgaaagcc | ggggccgacg | tggtccggct | gaatttctcc | 120 |
| catggtacgg | cggaggaaca | ccgcatccgc | gccgagcggg | tgcggaaaat | cagccggcgc | 180 |
| atgcagcgtt | atgtggccat | cctggccgat | ctgcaggggc | caagatccg | tatcgcccgc | 240 |
| ttcaagggcg | accgccaggt | cgtgctggag | gaaggccagc | ctttcgacct | ggacaccgcc | 300 |
| tttccgccgg | atcagggcga | tgaaacccag | gttggctgcg | cctatgaggc | gcttccgacg | 360 |
| gacgtcgaag | cgggcgacac | cttgctgctc | aacgacggtc | tgatcgagct | caaggtcaaa | 420 |
| tcggtcgaag | gaacccgcgt | cagatgcgtc | gtcaccgtcg | gcggcgtgct | gtccaaccac | 480 |
| aaaggcatca | acaagctcgg | cggcggtctc | tcggcgccgg | ccctgaccga | aaaggacaag | 540 |
| gcggatctga | agactgccgt | ggagatcggg | gccgactatc | tggcgatttc | ctttccgcgt | 600 |
| tcgaaggaag | acatgctgga | agcccgcgaa | ctgttgcacc | gggccggcag | tcacatgggg | 660 |
| ctggtggcca | aggtcgagcg | tgcggaagcc | atcaaggatg | tgtgatcga | agggatcatc | 720 |
| gacgcttccg | acgccatcat | ggtggcgcgc | ggcgacctgg | cgtggagat | cggcgacgcc | 780 |
| cgtctgccac | atgagcagaa | gaggctgatc | cgcttggcac | gcagccgcaa | caaggtcgtc | 840 |
| atcacggcca | cccagatgat | ggagtcgatg | atcgagaatc | ctttgccgac | gcgggccgag | 900 |
| gtctcggacg | tggccaacgc | cgtgatcgac | ggcaccgatg | ccgtgatgct | gtccgccgaa | 960 |
| accgccacgg | ggaagtttcc | ggaccgtacc | gtggcggcga | tggtgcgggt | ttgcaaggaa | 1020 |
| gcggaaaaat | acccgcggac | gcgccaatcg | agccaccgca | tggacgagaa | attccaccgc | 1080 |
| atcgacgagg | ccatcgccat | gtcggcgatg | tatatcgcca | accacctgcc | ggtccgggcc | 1140 |
| atcggtgcct | tgacggaatc | ggggtcgacg | cccctgtgga | tgtcgcgcat | cagttccggc | 1200 |
| atcccgatct | tcgccctcac | gccgcatgag | gcggtgtgtc | ggcgggtgac | gctgttccgg | 1260 |
| ggggtctatc | cgatttttt | caacgagcgc | gccatctcgg | atcaccacgt | gctgaaccgg | 1320 |
| gcgatcgccg | aagaattcct | taaacgcaat | ctggtgaaga | tggacgatct | ggtcatcatg | 1380 |
| accaaaggtg | atttgaccgg | ccgcaccggt | ggcaccaacg | ccttgaagat | atcgcgcatc | 1440 |
| agcgacgtca | tcgccgccgc | gccttga | | | | 1467 |

<210> SEQ ID NO 6
<211> LENGTH: 1305
<212> TYPE: DNA
<213> ORGANISM: Escherichia coli
<220> FEATURE:
<223> OTHER INFORMATION: Isocitrate Lyase

<400> SEQUENCE: 6

| | | | | | |
|---|---|---|---|---|---|
| atgaaaaccc | gtacacaaca | aattgaagaa | ttacagaaag | agtggactca | accgcgttgg | 60 |
| gaaggcatta | ctcgcccata | cagtgcggaa | gatgtggtga | attacgcgg | ttcagtcaat | 120 |
| cctgaatgca | cgctggcgca | actgggcgca | gcgaaaatgt | ggcgtctgct | gcacggtgag | 180 |
| tcgaaaaaag | gctacatcaa | cagcctcggc | gcactgactg | gcggtcaggc | gctgcaacag | 240 |
| gcgaaagcgg | gtattgaagc | agtctatctg | tcgggatggc | aggtagcggc | ggacgctaac | 300 |
| ctggcggcca | gcatgtatcc | ggatcagtcg | ctctatccgg | caaactcggt | gccagctgtg | 360 |

```
gtggagcgga tcaacaacac cttccgtcgt gccgatcaga tccaatggtc cgcgggcatt    420
gagccgggcg atccgcgcta tgtcgattac ttcctgccga tcgttgccga tgcggaagcc    480
ggttttggcg tgtcctgaa tgcctttgaa ctgatgaaag cgatgattga agccggtgca    540
gcggcagttc acttcgaaga tcagctggcg tcagtgaaga aatgcggtca catgggcggc    600
aaagttttag tgccaactca ggaagctatt cagaaactgg tcgcggcgcg tctggcagct    660
gacgtgacgg gcgttccaac cctgctggtt gcccgtaccg atgctgatgc ggcggatctg    720
atcacctccg attgcgaccc gtatgacagc gaatttatta ccggcgagcg taccagtgaa    780
ggcttcttcc gtactcatgc gggcattgag caagcgatca gccgtggcct ggcgtatgcg    840
ccatatgctg acctggtctg tgtgaaacc tccacgccgg atctggaact ggcgcgtcgc    900
tttgcacaag ctatccacgc gaaatatccg ggcaaactgc tggcttataa ctgctcgccg    960
tcgttcaact ggcagaaaaa cctcgacgac aaaactattg ccagcttcca gcagcagctg   1020
tcggatatgg gctacaagtt ccagttcatc cccctggcag gtatccacag catgtggttc   1080
aacatgtttg acctggcaaa cgcctatgcc cagggcgagg gtatgaagca ctacgttgag   1140
aaagtgcagc agccggaatt tgccgccgcg aaagatggct ataccttcgt atctcaccag   1200
caggaagtgg gtacaggtta cttcgataaa gtgacgacta ttattcaggg cggcacgtct   1260
tcagtcaccg cgctgaccgg ctccactgaa gaatcgcagt tctaa               1305

<210> SEQ ID NO 7
<211> LENGTH: 297
<212> TYPE: DNA
<213> ORGANISM: Escherichia coli
<220> FEATURE:
<223> OTHER INFORMATION: Cityl CoA lyase; citD

<400> SEQUENCE: 7
atgaaaataa accagcccgc cgttgcaggc acccttgagt ctggggatgt gatgatacgc     60
atcgccccac tcgatacgca ggatatcgac ctgcaaatca atagcagcgt tgagaaacag    120
tttggcgatg caattcgcac caccattctg gacgttctcg cccgctacaa cgtgcgcggc    180
gtacagctga atgtcgatga caaaggcgca ctggactgca ttttacgtgc acgactggaa    240
gccctgctgg cacgcgccag cggtatcccg gctctgccat gggaggattg ccaatga       297

<210> SEQ ID NO 8
<211> LENGTH: 1602
<212> TYPE: DNA
<213> ORGANISM: Escherichia coli
<220> FEATURE:
<223> OTHER INFORMATION: Malate Synthase A

<400> SEQUENCE: 8
atgactgaac aggcaacaac aaccgatgaa ctggctttca aaggccgta tggcgagcag     60 gagaagcaaa ttcttactgc cgaagcggta gaatttctga ctgagctggt gacgcatttt    120
acgccacaac gcaataaact tctggcagcg cgcattcagc agcagcaaga tattgataac    180
ggaacgttgc ctgattttat ttcggaaaca gcttccattc gcgatgctga ttggaaaatt    240
cgcgggattc ctgcggactt agaagaccgc cgcgtagaga taactggccc ggtagagcgc    300
aagatggtga tcaacgcgct caacgccaat gtgaaagtct ttatggccga tttcgaagat    360
tcactggcac cagactggaa caaagtgatc gacgggcaaa ttaacctgcg tgatgcggtt    420
aacggcacca tcagttacac caatgaagca ggcaaaattt accagctcaa gcccaatcca    480
```

```
gcggttttga tttgtcgggt acgcggtctg cacttgccgg aaaaacatgt cacctggcgt      540
ggtgaggcaa tccccggcag cctgtttgat tttgcgctct atttcttcca caactatcag      600
gcactgttgg caaagggcag tggtccctat ttctatctgc gaaaaccca gtcctggcag       660 gaagcggcct ggtggagcga agtcttcagc tatgcagaag atcgcttaa tctgccgcgc       720 ggcaccatca aggcgacgtt gctgattgaa acgctgcccg ccgtgttcca gatggatgaa      780
atccttcacg cgctgcgtga ccatattgtt ggtctgaact gcggtcgttg ggattacatc      840
ttcagctata tcaaaacgtt gaaaaactat cccgatcgcg tcctgccaga cagacaggca      900
gtgacgatgg ataaaccatt cctgaatgct tactcacgcc tgttgattaa aacctgccat      960
aaacgcggtg cttttgcgat gggcggcatg gcggcgttta ttccgagcaa agatgaagag     1020
cacaataacc aggtgctcaa caaagtaaaa gcggataaat cgctggaagc caataacggt     1080
cacgatggca catggatcgc tcacccaggc cttgcggaca cggcaatggc ggtattcaac     1140
gacattctcg gctcccgtaa aaatcagctt gaagtgatgc gcgaacaaga cgcgccgatt     1200
actgccgatc agctgctggc accttgtgat ggtgaacgca ccgaagaagg tatgcgcgcc     1260
aacattcgcg tggctgtgca gtacatcgaa gcgtggatct ctggcaacgg ctgtgtgccg     1320
atttatggcc tgatggaaga tgcggcgacg gctgaaattt cccgtacctc gatctggcag     1380
tggatccatc atcaaaaaac gttgagcaat ggcaaaccgg tgaccaaagc cttgttccgc     1440
cagatgctgg cgaagagat gaaagtcatt gccagcgaac tgggcgaaga acgtttctcc     1500
caggggcgtt ttgacgatgc cgcacgcttg atggaacaga tcaccacttc cgatgagtta     1560
attgatttcc tgaccctgcc aggctaccgc ctgttagcgt aa                        1602

<210> SEQ ID NO 9
<211> LENGTH: 870
<212> TYPE: DNA
<213> ORGANISM: Escherichia coli
<220> FEATURE:
<223> OTHER INFORMATION: Succinyl CoA synthetase; sucD

<400> SEQUENCE: 9
atgtccattt taatcgataa aaacaccaag gttatctgcc agggctttac cggtagccag       60
gggactttcc actcagaaca ggccattgca tacggcacta aaatggttgg cggcgtaacc      120
ccaggtaaag gcggcaccac ccacctcggc ctgccggtgt caacaccgt gcgtgaagcc       180 gttgctgcca ctggcgctac cgcttctgtt atctacgtac cagcaccgtt ctgcaaagac      240
tccattctgg aagccatcga cgcaggcatc aaactgatta tcaccatcac tgaaggcatc      300
ccgacgctgg atatgctgac cgtgaaagtg aagctggatg aagcaggcgt tcgtatgatc      360
ggcccgaact gccagggcgt tatcactccg ggtgaatgca aaatcggtat ccagcctggt      420
cacattcaca accgggtaa agtgggtatc gtttcccgtt ccggtacact gacctatgaa      480
gcggttaaac agaccaccgga ttacggtttc ggtcagtcga cctgtgtcgg tatcggcggt      540
gacccgatcc cgggctctaa ctttatcgac attctcgaaa tgttcgaaaa agatccgcag      600
accgaagcga tcgtgatgat cggtgagatc ggcggtagcg ctgaagaaga agcagctgcg      660
tacatcaaag agcacgttac caagccagtt gtgggttaca tcgctggtgt gactgcgccg      720
aaaggcaaac gtatgggcca cgcgggtgcc atcattgccg gtgggaaagg gactgcggat      780
gagaaattcg ctgctctgga agccgcaggc gtgaaaaccg ttcgcagcct ggcggatatc      840
ggtgaagcac tgaaaactgt tctgaaataa                                        870
```

<210> SEQ ID NO 10
<211> LENGTH: 1809
<212> TYPE: DNA
<213> ORGANISM: Escherichia coli
<220> FEATURE:
<223> OTHER INFORMATION: Fumarate Reductase; frdA

<400> SEQUENCE: 10

| | | | | | |
|---|---|---|---|---|---|
| gtgcaaacct | ttcaagccga | tcttgccatt | gtaggcgccg | gtggcgcggg | attacgtgct | 60 |
| gcaattgctg | ccgcgcaggc | aaatccgaat | gcaaaaatcg | cactaatctc | aaaagtatac | 120 |
| ccgatgcgta | gccataccgt | tgctgcagaa | ggggctccg | ccgctgtcgc | gcaggatcat | 180 |
| gacagcttcg | aatatcactt | tcacgataca | gtagcgggtg | gcgactggtt | gtgtgagcag | 240 |
| gatgtcgtgg | attatttcgt | ccaccactgc | ccaaccgaaa | tgacccaact | ggaactgtgg | 300 |
| ggatgcccat | ggagccgtcg | cccggatggt | agcgtcaacg | tacgtcgctt | cggcggcatg | 360 |
| aaaatcgagc | gcacctggtt | cgccgccgat | aagaccggct | tccatatgct | gcacacgctg | 420 |
| ttccagacct | ctctgcaatt | cccgcagatc | cagcgttttg | acgaacattt | cgtgctggat | 480 |
| attctggttg | atgatggtca | tgttcgcggc | ctggtagcaa | tgaacatgat | ggaaggcacg | 540 |
| ctggtgcaga | tccgtgctaa | cgcggtcgtt | atggctactg | gcggtgcggg | tcgcgtttat | 600 |
| cgttacaaca | ccaacggcgg | catcgttacc | ggtgacggta | tgggtatggc | gctaagccac | 660 |
| ggcgttccgc | tgcgtgacat | ggaattcgtt | cagtatcacc | caaccggtct | gccaggttcc | 720 |
| ggtatcctga | tgaccgaagg | ttgccgcggt | gaaggcggta | ttctggtcaa | caaaaatggc | 780 |
| taccgttatc | tgcaagatta | cggcatgggc | ccggaaactc | cgctgggcga | ccgaaaaac | 840 |
| aaatatatgg | aactgggtcc | acgcgacaaa | gtctctcagg | ccttctggca | cgaatggcgt | 900 |
| aaaggcaaca | ccatctccac | gccgcgtggc | gatgtggttt | atctcgactt | gcgtcacctc | 960 |
| ggcgagaaaa | aactgcatga | acgtctgccg | ttcatctgcg | aactggcgaa | agcgtacgtt | 1020 |
| ggcgtcgatc | cggttaaaga | accgattccg | gtacgtccga | ccgcacacta | ccatggggc | 1080 |
| ggtatcgaaa | ccgatcagaa | ctgtgaaacc | cgcattaaag | gtctgttcgc | cgtgggtgaa | 1140 |
| tgttcctctg | ttggtctgca | cggtgcaaac | cgtctgggtt | ctaactccct | ggcggaactg | 1200 |
| gtggtcttcg | gccgtctggc | cggtgaacaa | gcgacagagc | gtgcagcaac | tgccggtaat | 1260 |
| ggcaacgaag | cggcaattga | agcgcaggca | gctggcgttg | aacaacgtct | gaaagatctg | 1320 |
| gttaaccagg | atggcggcga | aaactgggcg | aagatccgcg | acgaaatggg | cctggctatg | 1380 |
| gaagaaggct | gcggtatcta | ccgtacgccg | gaactgatgc | agaaaaccat | cgacaagctg | 1440 |
| gcagagctgc | aggaacgctt | caagcgcgtg | cgcatcaccg | acacttccag | cgtgttcaac | 1500 |
| accgacctgc | tctacaccat | tgaactgggc | cacggtctga | cgttgctga | atgtatggcg | 1560 |
| cactccgcaa | tggcacgtaa | agagtcccgc | ggcgcgcacc | agcgtctgga | cgaaggttgc | 1620 |
| accgagcgtg | acgacgtcaa | cttcctcaaa | cacaccctcg | ccttccgcga | tgctgatggc | 1680 |
| acgactcgcc | tggagtacag | cgacgtgaag | attactacgc | tgccgccagc | taaacgcgtt | 1740 |
| tacggtggcg | aagcggatgc | agccgataag | gcggaagcag | ccaataagaa | ggagaaggcg | 1800 |
| aatggctga | | | | | 1809 |

<210> SEQ ID NO 11
<211> LENGTH: 1191
<212> TYPE: DNA
<213> ORGANISM: Escherichia coli
<220> FEATURE:
<223> OTHER INFORMATION: Aspartate transaminase

<400> SEQUENCE: 11

```
atgtttgaga acattaccgc cgctcctgcc gacccgattc tgggcctggc cgatctgttt      60
cgtgccgatg aacgtcccgg caaaattaac ctcgggattg gtgtctataa agatgagacg     120
ggcaaaaccc cggtactgac cagcgtgaaa aaggctgaac agtatctgct cgaaaatgaa     180
accaccaaaa attacctcgg cattgacggc atccctgaat ttggtcgctg cactcaggaa     240
ctgctgtttg gtaaaggtag cgccctgatc aatgacaaac gtgctcgcac ggcacagact     300
ccggggggca ctggcgcact acgcgtggct gccgatttcc tggcaaaaaa taccagcgtt     360
aagcgtgtgt gggtgagcaa cccaagctgg ccgaaccata gagcgtctt taactctgca      420
ggtctggaag ttcgtgaata cgcttattat gatgcggaaa atcacactct tgacttcgat     480
gcactgatta acagcctgaa tgaagctcag gctggcgacg tagtgctgtt ccatggctgc     540
tgccataacc caaccggtat cgaccctacg ctggaacaat ggcaaacact ggcacaactc     600
tccgttgaga aaggctggtt accgctgttt gacttcgctt accagggttt tgcccgtggt     660
ctggaagaag atgctgaagg actgcgcgct ttcgcggcta tgcataaaga gctgattgtt     720
gccagttcct actctaaaaa ctttggcctg tacaacgagc gtgttggcgc ttgtactctg     780
gttgctgccg acagtgaaac cgttgatcgc gcattcagcc aaatgaaagc ggcgattcgc     840
gctaactact ctaacccacc agcacacggc gcttctgttg ttgccaccat cctgagcaac     900
gatgcgttac gtgcgatttg gaacaagagc tgactgata tgcgccagcg tattcagcgt      960
atgcgtcagt tgttcgtcaa tacgctgcag gaaaaaggcg caaaccgcga cttcagcttt    1020
atcatcaaac agaacggcat gttctccttc agtggcctga caaagaaca agtgctgcgt      1080
ctgcgcgaag agtttggcgt atatgcggtt gcttctggtc gcgtaaatgt ggccgggatg    1140
acaccagata acatggctcc gctgtgcgaa gcgattgtgg cagtgctgta a             1191
```

<210> SEQ ID NO 12
<211> LENGTH: 312
<212> TYPE: PRT
<213> ORGANISM: Escherichia coli
<220> FEATURE:
<223> OTHER INFORMATION: Malate dehydrogenase

<400> SEQUENCE: 12

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140
```

```
Gly Val Thr Thr Leu Asp Ile Ile Arg Ser Asn Thr Phe Val Ala Glu
145                 150                 155                 160

Leu Lys Gly Lys Gln Pro Gly Glu Val Glu Pro Val Ile Gly Gly
            165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
        195                 200                 205

Ala Gly Thr Glu Val Val Glu Ala Lys Ala Gly Gly Ser Ala Thr
            210                 215                 220

Leu Ser Met Gly Gln Ala Ala Arg Phe Gly Leu Ser Leu Val Arg
225                 230                 235                 240

Ala Leu Gln Gly Glu Gln Gly Val Val Glu Cys Ala Tyr Val Glu Gly
            245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
290                 295                 300

Leu Gly Glu Glu Phe Val Asn Lys
305                 310

<210> SEQ ID NO 13
<211> LENGTH: 1096
<212> TYPE: PRT
<213> ORGANISM: Pseudomonas aeruginosa
<220> FEATURE:
<223> OTHER INFORMATION: Pyruvate Carboxylase

<400> SEQUENCE: 13

Met Thr Ala Pro Pro Phe Asn Ala Leu Leu Ile Ala Asn Arg Gly Glu
1               5                   10                  15

Ile Ala Ile Arg Ile Ala Arg Ala Cys Ala Asp Leu Gly Ile Arg Ser
            20                  25                  30

Val Ala Val Phe Ala Glu Asp Asp Ala Ala Ser Leu His Val Arg Lys
        35                  40                  45

Ala Asp Val Ala Leu Pro Leu Ala Gly Arg Gly Val Ala Ala Tyr Leu
    50                  55                  60

Asp Met Asp Arg Leu Val Ala Leu Ala Leu Glu Gln Gly Cys Glu Ala
65                  70                  75                  80

Ile His Pro Gly Tyr Gly Phe Leu Ala Glu Asn Gly Glu Phe Ala Arg
                85                  90                  95

Arg Cys Gln Arg Ala Gly Ile His Phe Val Gly Pro Gln Ala Glu Val
            100                 105                 110

Leu Asp Leu Leu Gly Asp Lys Ala Ala Arg Ala Leu Ala Glu Arg
        115                 120                 125

Leu Glu Val Pro Leu Val Ala Gly Ile Asn Arg Ala Val Ser Val Glu
    130                 135                 140

Glu Ala Glu Ala Phe Leu Glu Gly Leu Gly Asp Gly Ala Ala Val Met
145                 150                 155                 160

Leu Lys Ala Leu Ala Gly Gly Gly Arg Gly Met Arg Ala Val Glu
            165                 170                 175

Glu Val Ala Gln Leu Ala Asp Ala Tyr Arg Arg Cys Arg Ala Glu Ala
        180                 185                 190
```

```
Gln Ala Ala Phe Gly Arg Asp Glu Leu Tyr Val Glu Gln Arg Val Ala
            195                 200                 205
Arg Ala Arg His Ile Glu Val Gln Val Leu Gly Asp Gly Ser Gly Ala
    210                 215                 220
Val Ser His Leu Trp Glu Arg Asp Cys Ser Leu Gln Arg Arg Gln Gln
225                 230                 235                 240
Lys Leu Leu Glu Ile Ala Pro Ser Pro Asp Leu Pro Glu Ala Thr Arg
                245                 250                 255
Glu Ala Leu Ile Asp Cys Ala Leu Arg Met Ala Gly Ala Val Arg Tyr
            260                 265                 270
Arg Gly Ile Gly Thr Phe Glu Phe Leu Val Asp Glu Arg Pro Gly
        275                 280                 285
His Phe Tyr Phe Met Glu Ala Asn Pro Arg Ile Gln Val Glu His Thr
    290                 295                 300
Val Thr Glu Glu Val Thr Gly Val Asp Leu Leu His Ala Gln Leu Arg
305                 310                 315                 320
Leu Ala Ala Gly Met Glu Leu Ala Ala Leu Gly Leu Glu Arg Pro Pro
                325                 330                 335
Ala Ile Gly Gly Cys Ala Val Gln Leu Arg Ile Asn Leu Glu Thr Leu
            340                 345                 350
Ala Val Asp Gly Ser Ala Arg Pro Ala Val Gly Thr Ile Gly Ala Tyr
        355                 360                 365
Glu Pro Pro Ser Gly Pro Gly Leu Arg Val Asp Gly Tyr Gly Tyr Ala
    370                 375                 380
Gly Tyr Arg Val Ser Pro Ser Tyr Asp Ser Leu Leu Ala Lys Leu Val
385                 390                 395                 400
Val Arg Gly Ala Asp Tyr Pro Ala Ala Leu Arg Arg Ala Tyr Arg Ala
                405                 410                 415
Leu Cys Glu Phe Arg Leu Glu Gly Val Ala Ser Asn Leu Asp Leu Leu
            420                 425                 430
Arg Asn Leu Leu His Pro Ala Val Gln Ala Asn Arg Val Asp Thr
        435                 440                 445
Arg Phe Val Glu Ser His Leu Glu Thr Leu Leu Ala Pro Ile Pro Ala
    450                 455                 460
Ser His Pro Arg Leu Arg Ala Glu Cys Pro Leu Ala Glu Asp Ala Ala
465                 470                 475                 480
Pro Ala Arg Val Glu Ala Pro Leu Gly Ser Leu Pro Leu Ser Ala Pro
                485                 490                 495
Ser Ser Gly Val Leu Val Ala Leu Glu Val Ala Glu Gly Glu Arg Val
            500                 505                 510
Arg Ala Gly Gln Arg Val Ala Ile Leu Glu Ala Met Lys Met Glu Phe
        515                 520                 525
Glu Val Lys Ala Pro Gly Gly Gly Ile Val Arg Leu Ala Ala Ser
    530                 535                 540
Leu Gly Glu Pro Leu Glu Glu Gly Ala Thr Leu Leu Phe Leu Glu Pro
545                 550                 555                 560
Thr Glu Asp Asp Glu Gln Ala Pro Thr Glu Gln Ala Leu Asp Leu
                565                 570                 575
Ala His Ile Arg Ala Asp Leu Ala Glu Val Leu Glu Arg Gln Ala Ala
            580                 585                 590
Leu Gly Asp Glu Arg Arg Pro Gln Ala Leu Ala Arg Arg Lys Thr
        595                 600                 605
Gly Gln Arg Thr Ala Arg Glu Asn Val Leu Asp Leu Leu Asp Glu Gly
```

-continued

```
            610                 615                 620
Ser Phe Ser Glu Tyr Gly Gly Phe Ala Leu Ala Ala Gln Arg Arg
625                 630                 635                 640

Arg Ser Ala Glu Glu Leu Leu Glu Leu Ser Pro Ala Asp Gly Leu Val
                645                 650                 655

Ala Gly Thr Gly Thr Val Gly Ala Ala Ser Phe Gly Val Gln Ala Ala
                660                 665                 670

Arg Cys Leu Val Leu Ala Tyr Asp Tyr Thr Val Phe Ala Gly Thr Gln
                675                 680                 685

Gly Val Met Asn His Lys Lys Thr Asp Arg Leu Leu Gly Leu Ala Glu
                690                 695                 700

Gln Trp Arg Leu Pro Leu Val Leu Phe Ala Glu Gly Gly Gly Arg
705                 710                 715                 720

Pro Gly Asp Thr Asp Phe Val Gly Val Ala Gly Leu Asp Cys His Thr
                725                 730                 735

Phe Val Gly Met Ala Arg Leu Ser Gly Leu Val Pro Leu Val Gly Val
                740                 745                 750

Val Ser Gly Arg Cys Phe Ala Gly Asn Ala Ala Leu Leu Gly Cys Cys
                755                 760                 765

Asp Val Ile Ile Ala Thr Arg Asp Ala Thr Ile Gly Met Ala Gly Pro
770                 775                 780

Ala Met Ile Glu Gly Gly Gly Leu Gly Arg Phe Ala Ala Glu Val
785                 790                 795                 800

Gly Pro Thr Gly Val Gln Gly Pro Asn Gly Val Ile Asp Val Leu Val
                805                 810                 815

Glu Asp Glu Ala Glu Ala Val Ala Val Ala Arg Arg Tyr Leu Gly Tyr
                820                 825                 830

Phe Gln Gly Pro Leu Pro Asp Trp Ser Cys Ala Asp Gln Arg Glu Leu
                835                 840                 845

Arg His Leu Val Pro Glu Asn Arg Leu Arg Ala Tyr Asp Ile Arg Gln
850                 855                 860

Ala Ile Glu Val Leu Ala Asp Arg Gly Ser Val Leu Glu Leu Arg Arg
865                 870                 875                 880

Gln Phe Ala Pro Gly Leu Val Thr Ala Leu Leu Arg Ile Glu Gly Arg
                885                 890                 895

Ala Phe Gly Leu Ile Ala Asn Asn Pro Gly His Leu Gly Gly Ala Ile
                900                 905                 910

Asp Ala Ala Ala Gly Asp Lys Ala Ala Arg Phe Met Gln Leu Cys Asp
                915                 920                 925

Ala Phe Asp Ile Pro Ile Val Ser Leu Cys Asp Thr Pro Gly Phe Met
930                 935                 940

Val Gly Pro Glu Ala Glu Lys Gln Ala Thr Val Arg His Val Ser Arg
945                 950                 955                 960

Met Phe Val Ser Ala Ala Ser Leu Thr Val Pro Phe Phe Thr Val Val
                965                 970                 975

Leu Arg Lys Gly Tyr Gly Leu Gly Ala Gln Ala Met Ala Ala Gly Ser
                980                 985                 990

Phe His Ser Pro Leu Phe Thr Val Ala Trp Pro Ser Gly Glu Phe Gly
                995                 1000                1005

Ala Met Gly Leu Glu Gly Ala Val Arg Leu Gly Phe Ala Lys Glu
            1010                1015                1020

Leu Ala Ala Glu Glu Asp Pro Gln Arg Arg Glu Ala Leu Phe Arg
            1025                1030                1035
```

```
Gly Met Val Asp Lys Ala Tyr Arg Asn Gly Lys Ala Leu Asn Met
    1040                1045                1050

Ala Ser Tyr Leu Glu Ile Asp Ala Val Ile Asp Pro Ala Glu Thr
    1055                1060                1065

Arg Ala Trp Leu Leu Arg Gly Leu Ala Val Ala Gly Glu Pro Val
    1070                1075                1080

Pro Arg Ala Gly Arg Lys Arg Pro Phe Val Asp Thr Trp
    1085                1090                1095

<210> SEQ ID NO 14
<211> LENGTH: 883
<212> TYPE: PRT
<213> ORGANISM: Escherichia coli
<220> FEATURE:
<223> OTHER INFORMATION: Phosphoenol pyruvate carboxylase

<400> SEQUENCE: 14

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
290                 295                 300
```

```
Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
            325                 330                 335

Glu Glu Leu Pro Lys Pro Glu Gly Leu Leu Thr Gln Asn Glu Glu Leu
        340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
        370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
            405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
            485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
            565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
            645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720
```

```
Trp Thr Gln Asn Arg Leu Met Leu Pro Ala Trp Leu Gly Ala Gly Thr
            725                 730                 735

Ala Leu Gln Lys Val Val Glu Asp Gly Lys Gln Ser Glu Leu Glu Ala
        740                 745                 750

Met Cys Arg Asp Trp Pro Phe Phe Ser Thr Arg Leu Gly Met Leu Glu
    755                 760                 765

Met Val Phe Ala Lys Ala Asp Leu Trp Leu Ala Glu Tyr Tyr Asp Gln
770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly

<210> SEQ ID NO 15
<211> LENGTH: 420
<212> TYPE: PRT
<213> ORGANISM: Methylococcus capsulatus Bath
<220> FEATURE:
<223> OTHER INFORMATION: Phosphoenol pyruvate carboxylase

<400> SEQUENCE: 15

Met Ala Ala Arg Asn Ala Phe Tyr Ala Gln Ser Gly Gly Val Thr Ala
1               5                   10                  15

Val Ile Asn Ala Ser Ala Cys Gly Val Leu Glu Thr Ala Arg Gln Tyr
            20                  25                  30

Pro Asp Arg Ile Gly Thr Val Tyr Ala Gly Arg Asn Gly Ile Val Gly
        35                  40                  45

Ala Leu Thr Glu Asp Leu Ile Asp Thr Gly Gln Glu Ser Ala Glu Ala
    50                  55                  60

Ile Ala Ala Leu Arg His Thr Pro Ser Gly Ala Phe Gly Ser Cys Arg
65                  70                  75                  80

Tyr Lys Leu Lys Gly Leu Glu Glu Asn Arg Ala Gln Tyr Glu Arg Leu
                85                  90                  95

Ile Glu Val Phe Arg Ala His Asp Ile Gly Tyr Phe Phe Tyr Asn Gly
            100                 105                 110

Gly Gly Asp Ser Ala Asp Thr Cys Leu Lys Val Ser Gln Leu Ser Glu
        115                 120                 125

Lys Leu Gly Tyr Pro Leu Gln Ala Val His Ile Pro Lys Thr Val Asp
    130                 135                 140

Asn Asp Leu Pro Ile Thr Asp Cys Cys Pro Gly Phe Gly Ser Val Ala
145                 150                 155                 160

Lys Tyr Ile Ala Val Ser Val Arg Glu Ala Ser Phe Asp Val Arg Ser
                165                 170                 175

Met Ala Ala Thr Ser Thr Cys Ile Phe Val Leu Glu Val Met Gly Arg
            180                 185                 190

His Ala Gly Trp Ile Ala Ala Ala Gly Gly Leu Ala Ser Asp Glu Arg
```

```
                195                 200                 205
His Glu Leu Ala Leu Val Ile Leu Phe Pro Glu Gln Val Phe Asp Pro
    210                 215                 220

Glu Arg Phe Leu Arg Ala Val Asp Glu Lys Val Arg Ser His Gly Tyr
225                 230                 235                 240

Cys Ser Val Val Val Ser Glu Gly Ile Arg Gly Ala Asp Gly Arg Phe
                245                 250                 255

Val Ala Glu Ser Gly Ser Arg Asp Val Phe Gly His Ala Arg Leu Gly
            260                 265                 270

Gly Val Ala Pro Val Ile Ala Asp Leu Ile Lys Glu Arg Leu Gly Tyr
        275                 280                 285

Lys Tyr His Trp Ala Val Ala Asp Tyr Leu Gln Arg Ala Ala Arg His
    290                 295                 300

Ile Ala Ser Arg Thr Asp Val Glu Gln Ala Tyr Ala Val Gly Lys Ala
305                 310                 315                 320

Gly Val Glu Met Ala Leu Lys Gly Leu Ser Ala Val Met Pro Ala Ile
                325                 330                 335

Val Arg Thr Ser Asp Ser Pro Tyr Arg Trp Glu Ile Thr Ala Ala Ser
            340                 345                 350

Leu Ala Glu Val Ala Asn Val Glu Lys Lys Met Pro Leu Glu Phe Ile
        355                 360                 365

Ser Ala Asp Gly Phe Gly Ile Thr Glu Ala Cys Arg Arg Tyr Leu Arg
    370                 375                 380

Pro Leu Ile Glu Gly Glu Asp Tyr Pro Pro Tyr Ala Gly Gly Leu Pro
385                 390                 395                 400

Asp Tyr Val Thr Leu Cys Asn Val Ala Val Pro Lys Lys Leu Ala Ala
                405                 410                 415

Ser Phe Ser Val
            420

<210> SEQ ID NO 16
<211> LENGTH: 488
<212> TYPE: PRT
<213> ORGANISM: Escherichia coli
<220> FEATURE:
<223> OTHER INFORMATION: Pyruvate Kinase

<400> SEQUENCE: 16

Met Thr Arg Gly Ile Arg Arg Thr Lys Ile Ile Ala Thr Leu Gly Pro
1               5                   10                  15

Ala Ser Glu Ser Pro Glu Met Leu Glu Arg Ile Leu Lys Ala Gly Ala
            20                  25                  30

Asp Val Val Arg Leu Asn Phe Ser His Gly Thr Ala Glu Glu His Arg
        35                  40                  45

Ile Arg Ala Glu Arg Val Arg Glu Ile Ser Arg Arg Met Gln Arg Tyr
    50                  55                  60

Val Ala Ile Leu Ala Asp Leu Gln Gly Pro Lys Ile Arg Ile Ala Arg
65                  70                  75                  80

Phe Lys Gly Asp Arg Gln Val Val Leu Glu Glu Gly Gln Pro Phe Asp
                85                  90                  95

Leu Asp Thr Ala Phe Pro Pro Asp Gln Gly Asp Glu Thr Gln Val Gly
            100                 105                 110

Cys Ala Tyr Glu Ala Leu Pro Thr Asp Val Glu Ala Gly Asp Thr Leu
        115                 120                 125

Leu Leu Asn Asp Gly Leu Ile Glu Leu Lys Val Lys Ser Val Glu Gly
```

Thr Arg Val Arg Cys Val Val Thr Val Gly Gly Val Leu Ser Asn His
145                 150                 155                 160

Lys Gly Ile Asn Lys Leu Gly Gly Leu Ser Ala Pro Ala Leu Thr
            165                 170                 175

Glu Lys Asp Lys Ala Asp Leu Lys Thr Ala Val Glu Ile Gly Ala Asp
        180                 185                 190

Tyr Leu Ala Ile Ser Phe Pro Arg Ser Lys Glu Asp Met Leu Glu Ala
            195                 200                 205

Arg Glu Leu Leu His Arg Ala Gly Ser His Met Gly Leu Val Ala Lys
        210                 215                 220

Val Glu Arg Ala Glu Ala Ile Lys Asp Gly Val Ile Glu Gly Ile Ile
225                 230                 235                 240

Asp Ala Ser Asp Ala Ile Met Val Ala Arg Gly Asp Leu Gly Val Glu
            245                 250                 255

Ile Gly Asp Ala Arg Leu Pro His Glu Gln Lys Arg Leu Ile Arg Leu
            260                 265                 270

Ala Arg Ser Arg Asn Lys Val Val Ile Thr Ala Thr Gln Met Met Glu
        275                 280                 285

Ser Met Ile Glu Asn Pro Leu Pro Thr Arg Ala Glu Val Ser Asp Val
        290                 295                 300

Ala Asn Ala Val Ile Asp Gly Thr Asp Ala Val Met Leu Ser Ala Glu
305                 310                 315                 320

Thr Ala Thr Gly Lys Phe Pro Asp Arg Thr Val Ala Ala Met Val Arg
            325                 330                 335

Val Cys Lys Glu Ala Glu Lys Tyr Pro Arg Thr Arg Gln Ser Ser His
        340                 345                 350

Arg Met Asp Glu Lys Phe His Arg Ile Asp Glu Ala Ile Ala Met Ser
        355                 360                 365

Ala Met Tyr Ile Ala Asn His Leu Pro Val Arg Ala Ile Gly Ala Leu
        370                 375                 380

Thr Glu Ser Gly Ser Thr Pro Leu Trp Met Ser Arg Ile Ser Ser Gly
385                 390                 395                 400

Ile Pro Ile Phe Ala Leu Thr Pro His Glu Ala Val Cys Arg Arg Val
            405                 410                 415

Thr Leu Phe Arg Gly Val Tyr Pro Ile Phe Phe Asn Glu Arg Ala Ile
            420                 425                 430

Ser Asp His His Val Leu Asn Arg Ala Ile Ala Glu Glu Phe Leu Lys
        435                 440                 445

Arg Asn Leu Val Lys Met Asp Asp Leu Val Ile Met Thr Lys Gly Asp
    450                 455                 460

Leu Thr Gly Arg Thr Gly Gly Thr Asn Ala Leu Lys Ile Ser Arg Ile
465                 470                 475                 480

Ser Asp Val Ile Ala Ala Pro
            485

<210> SEQ ID NO 17
<211> LENGTH: 434
<212> TYPE: PRT
<213> ORGANISM: Escherichia coli
<220> FEATURE:
<223> OTHER INFORMATION: Isocitrate Lyase

<400> SEQUENCE: 17

Met Lys Thr Arg Thr Gln Gln Ile Glu Glu Leu Gln Lys Glu Trp Thr

-continued

```
1               5                   10                  15
Gln Pro Arg Trp Glu Gly Ile Thr Arg Pro Tyr Ser Ala Glu Asp Val
                20                  25                  30

Val Lys Leu Arg Gly Ser Val Asn Pro Glu Cys Thr Leu Ala Gln Leu
                35                  40                  45

Gly Ala Ala Lys Met Trp Arg Leu Leu His Gly Glu Ser Lys Lys Gly
         50                  55                  60

Tyr Ile Asn Ser Leu Gly Ala Leu Thr Gly Gln Ala Leu Gln Gln
 65                  70                  75                  80

Ala Lys Ala Gly Ile Glu Ala Val Tyr Leu Ser Gly Trp Gln Val Ala
                 85                  90                  95

Ala Asp Ala Asn Leu Ala Ala Ser Met Tyr Pro Asp Gln Ser Leu Tyr
                100                 105                 110

Pro Ala Asn Ser Val Pro Ala Val Val Glu Arg Ile Asn Asn Thr Phe
                115                 120                 125

Arg Arg Ala Asp Gln Ile Gln Trp Ser Ala Gly Ile Glu Pro Gly Asp
         130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
                180                 185                 190

Lys Lys Cys Gly His Met Gly Gly Lys Val Leu Val Pro Thr Gln Glu
                195                 200                 205

Ala Ile Gln Lys Leu Val Ala Ala Arg Leu Ala Ala Asp Val Thr Gly
         210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
                260                 265                 270

Ile Ser Arg Gly Leu Ala Tyr Ala Pro Tyr Ala Asp Leu Val Trp Cys
         275                 280                 285

Glu Thr Ser Thr Pro Asp Leu Glu Leu Ala Arg Arg Phe Ala Gln Ala
         290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
                340                 345                 350

Ala Gly Ile His Ser Met Trp Phe Asn Met Phe Asp Leu Ala Asn Ala
         355                 360                 365

Tyr Ala Gln Gly Glu Gly Met Lys His Tyr Val Glu Lys Val Gln Gln
         370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
                420                 425                 430
```

Gln Phe

<210> SEQ ID NO 18
<211> LENGTH: 98
<212> TYPE: PRT
<213> ORGANISM: Escherichia coli
<220> FEATURE:
<223> OTHER INFORMATION: Citryl CoA lyase; citD

<400> SEQUENCE: 18

```
Met Lys Ile Asn Gln Pro Ala Val Ala Gly Thr Leu Glu Ser Gly Asp
1               5                   10                  15

Val Met Ile Arg Ile Ala Pro Leu Asp Thr Gln Asp Ile Asp Leu Gln
            20                  25                  30

Ile Asn Ser Ser Val Glu Lys Gln Phe Gly Asp Ala Ile Arg Thr Thr
        35                  40                  45

Ile Leu Asp Val Leu Ala Arg Tyr Asn Val Arg Gly Val Gln Leu Asn
    50                  55                  60

Val Asp Asp Lys Gly Ala Leu Asp Cys Ile Leu Arg Ala Arg Leu Glu
65                  70                  75                  80

Ala Leu Leu Ala Arg Ala Ser Gly Ile Pro Ala Leu Pro Trp Glu Asp
                85                  90                  95

Cys Gln
```

<210> SEQ ID NO 19
<211> LENGTH: 533
<212> TYPE: PRT
<213> ORGANISM: Escherichia coli
<220> FEATURE:
<223> OTHER INFORMATION: Malate Synthase A

<400> SEQUENCE: 19

```
Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Gln Asp Ile Asp Asn Gly Thr Leu Pro
    50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Val Glu Ile Thr Gly
                85                  90                  95

Pro Val Glu Arg Lys Met Val Ile Asn Ala Leu Asn Ala Asn Val Lys
                100                 105                 110

Val Phe Met Ala Asp Phe Glu Asp Ser Leu Ala Pro Asp Trp Asn Lys
            115                 120                 125

Val Ile Asp Gly Gln Ile Asn Leu Arg Asp Ala Val Asn Gly Thr Ile
        130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
                180                 185                 190
```

Leu Tyr Phe Phe His Asn Tyr Gln Ala Leu Leu Ala Lys Gly Ser Gly
            195                 200                 205

Pro Tyr Phe Tyr Leu Pro Lys Thr Gln Ser Trp Gln Glu Ala Ala Trp
        210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
        290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
        355                 360                 365

Pro Gly Leu Ala Asp Thr Ala Met Ala Val Phe Asn Asp Ile Leu Gly
        370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
        450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510

Gln Ile Thr Thr Ser Asp Glu Leu Ile Asp Phe Leu Thr Leu Pro Gly
        515                 520                 525

Tyr Arg Leu Leu Ala
        530

<210> SEQ ID NO 20
<211> LENGTH: 289
<212> TYPE: PRT
<213> ORGANISM: Escherichia coli
<220> FEATURE:
<223> OTHER INFORMATION: Succinyl CoA synthetase; sucD

<400> SEQUENCE: 20

Met Ser Ile Leu Ile Asp Lys Asn Thr Lys Val Ile Cys Gln Gly Phe
1               5                   10                  15

```
Thr Gly Ser Gln Gly Thr Phe His Ser Glu Gln Ala Ile Ala Tyr Gly
             20                  25                  30

Thr Lys Met Val Gly Val Thr Pro Gly Lys Gly Thr Thr His
         35                  40                  45

Leu Gly Leu Pro Val Phe Asn Thr Val Arg Glu Ala Val Ala Thr
 50                      55                  60

Gly Ala Thr Ala Ser Val Ile Tyr Val Pro Ala Pro Phe Cys Lys Asp
 65                  70                  75                  80

Ser Ile Leu Glu Ala Ile Asp Ala Gly Ile Lys Leu Ile Ile Thr Ile
                 85                  90                  95

Thr Glu Gly Ile Pro Thr Leu Asp Met Leu Thr Val Lys Val Lys Leu
                100                 105                 110

Asp Glu Ala Gly Val Arg Met Ile Gly Pro Asn Cys Pro Gly Val Ile
            115                 120                 125

Thr Pro Gly Glu Cys Lys Ile Gly Ile Gln Pro Gly His Ile His Lys
130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
        195                 200                 205

Glu Ile Gly Gly Ser Ala Glu Glu Ala Ala Ala Tyr Ile Lys Glu
210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
        275                 280                 285

Lys

<210> SEQ ID NO 21
<211> LENGTH: 602
<212> TYPE: PRT
<213> ORGANISM: Escherichia coli
<220> FEATURE:
<223> OTHER INFORMATION: Fumarate Reductase; FrdA

<400> SEQUENCE: 21

Met Gln Thr Phe Gln Ala Asp Leu Ala Ile Val Gly Ala Gly Gly Ala
1               5                   10                  15

Gly Leu Arg Ala Ala Ile Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
```

```
                        85                90                 95
Leu Glu Leu Trp Gly Cys Pro Trp Ser Arg Arg Pro Asp Gly Ser Val
                100                105                110

Asn Val Arg Arg Phe Gly Gly Met Lys Ile Glu Arg Thr Trp Phe Ala
                115                120                125

Ala Asp Lys Thr Gly Phe His Met Leu His Thr Leu Phe Gln Thr Ser
                130                135                140

Leu Gln Phe Pro Gln Ile Gln Arg Phe Asp Glu His Phe Val Leu Asp
145                150                155                160

Ile Leu Val Asp Asp Gly His Val Arg Gly Leu Val Ala Met Asn Met
                165                170                175

Met Glu Gly Thr Leu Val Gln Ile Arg Ala Asn Ala Val Val Met Ala
                180                185                190

Thr Gly Gly Ala Gly Arg Val Tyr Arg Tyr Asn Thr Asn Gly Gly Ile
                195                200                205

Val Thr Gly Asp Gly Met Gly Met Ala Leu Ser His Gly Val Pro Leu
                210                215                220

Arg Asp Met Glu Phe Val Gln Tyr His Pro Thr Gly Leu Pro Gly Ser
225                230                235                240

Gly Ile Leu Met Thr Glu Gly Cys Arg Gly Glu Gly Ile Leu Val
                245                250                255

Asn Lys Asn Gly Tyr Arg Tyr Leu Gln Asp Tyr Gly Met Gly Pro Glu
                260                265                270

Thr Pro Leu Gly Glu Pro Lys Asn Lys Tyr Met Glu Leu Gly Pro Arg
                275                280                285

Asp Lys Val Ser Gln Ala Phe Trp His Glu Trp Arg Lys Gly Asn Thr
                290                295                300

Ile Ser Thr Pro Arg Gly Asp Val Val Tyr Leu Asp Leu Arg His Leu
305                310                315                320

Gly Glu Lys Lys Leu His Glu Arg Leu Pro Phe Ile Cys Glu Leu Ala
                325                330                335

Lys Ala Tyr Val Gly Val Asp Pro Val Lys Glu Pro Ile Pro Val Arg
                340                345                350

Pro Thr Ala His Tyr Thr Met Gly Gly Ile Glu Thr Asp Gln Asn Cys
                355                360                365

Glu Thr Arg Ile Lys Gly Leu Phe Ala Val Gly Glu Cys Ser Ser Val
                370                375                380

Gly Leu His Gly Ala Asn Arg Leu Gly Ser Asn Ser Leu Ala Glu Leu
385                390                395                400

Val Val Phe Gly Arg Leu Ala Gly Glu Gln Ala Thr Glu Arg Ala Ala
                405                410                415

Thr Ala Gly Asn Gly Asn Glu Ala Ala Ile Glu Ala Gln Ala Ala Gly
                420                425                430

Val Glu Gln Arg Leu Lys Asp Leu Val Asn Gln Asp Gly Gly Glu Asn
                435                440                445

Trp Ala Lys Ile Arg Asp Glu Met Gly Leu Ala Met Glu Glu Gly Cys
450                455                460

Gly Ile Tyr Arg Thr Pro Glu Leu Met Gln Lys Thr Ile Asp Lys Leu
465                470                475                480

Ala Glu Leu Gln Glu Arg Phe Lys Arg Val Arg Ile Thr Asp Thr Ser
                485                490                495

Ser Val Phe Asn Thr Asp Leu Leu Tyr Thr Ile Glu Leu Gly His Gly
                500                505                510
```

```
Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
    530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala Asn Gly
        595                 600

<210> SEQ ID NO 22
<211> LENGTH: 396
<212> TYPE: PRT
<213> ORGANISM: Escherichia coli
<220> FEATURE:
<223> OTHER INFORMATION: Aspartate transaminase

<400> SEQUENCE: 22

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45

Val Lys Lys Ala Glu Gln Tyr Leu Leu Glu Asn Glu Thr Thr Lys Asn
50                  55                  60

Tyr Leu Gly Ile Asp Gly Ile Pro Glu Phe Gly Arg Cys Thr Gln Glu
65                  70                  75                  80

Leu Leu Phe Gly Lys Gly Ser Ala Leu Ile Asn Asp Lys Arg Ala Arg
                85                  90                  95

Thr Ala Gln Thr Pro Gly Gly Thr Gly Ala Leu Arg Val Ala Ala Asp
            100                 105                 110

Phe Leu Ala Lys Asn Thr Ser Val Lys Arg Val Trp Val Ser Asn Pro
        115                 120                 125

Ser Trp Pro Asn His Lys Ser Val Phe Asn Ser Ala Gly Leu Glu Val
    130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
            180                 185                 190

Gln Trp Gln Thr Leu Ala Gln Leu Ser Val Glu Lys Gly Trp Leu Pro
        195                 200                 205

Leu Phe Asp Phe Ala Tyr Gln Gly Phe Ala Arg Gly Leu Glu Glu Asp
    210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
            260                 265                 270
```

```
Ser Gln Met Lys Ala Ala Ile Arg Ala Asn Tyr Ser Asn Pro Pro Ala
    275                 280                 285

His Gly Ala Ser Val Val Ala Thr Ile Leu Ser Asn Asp Ala Leu Arg
    290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
            340                 345                 350

Leu Thr Lys Glu Gln Val Leu Arg Leu Arg Glu Glu Phe Gly Val Tyr
        355                 360                 365

Ala Val Ala Ser Gly Arg Val Asn Val Ala Gly Met Thr Pro Asp Asn
    370                 375                 380

Met Ala Pro Leu Cys Glu Ala Ile Val Ala Val Leu
385                 390                 395

<210> SEQ ID NO 23
<211> LENGTH: 1533
<212> TYPE: DNA
<213> ORGANISM: Escherichia coli
<220> FEATURE:
<223> OTHER INFORMATION: Cityl CoA lyase; citF

<400> SEQUENCE: 23
```

| | | | | | |
|---|---|---|---|---|---|
| atgacgcaga | aaattgaaca | atctcaacga | caagaacggg | tagcggcctg | gaatcgtcgc | 60 |
| gctgaatgcg | atcttgccgc | tttccagaac | tcgccaaagc | aaacctacca | ggctgaaaaa | 120 |
| gcgcgcgatc | gcaaactgtg | cgccaacctg | gaagaagcga | ttcgtcgctc | tggtttacag | 180 |
| gacggcatga | cggtttcctt | ccatcacgct | ttccgtggcg | gtgacctgac | cgtcaatatg | 240 |
| gtgatggacg | tcatcgcgaa | gatgggcttt | aaaaaacctga | ccctggcgtc | cagctccctg | 300 |
| agtgattgcc | atgcgccgct | ggtagaacac | attcgccagg | gcgtggttac | ccgcatttat | 360 |
| acctccggcc | tgcgtggtcc | actggcggaa | gagatctccc | gtggtctgct | ggcagaaccg | 420 |
| gtgcagatcc | actctcacgg | cggtcgtgtg | catctggtac | agagcggcga | actgaatatc | 480 |
| gacgtggctt | cctcggcgt | cccgtcctgt | gatgaattcg | gtaatgccaa | cggctacacc | 540 |
| ggtaaagcct | gctgcggctc | cctcggctat | gcaatagttg | atgccgacaa | cgcaaaacag | 600 |
| gtcgtgatgc | ttaccgaaga | actgctgcct | tatccgcata | tccggcaag | cattgagcaa | 660 |
| gatcaggttg | atttgatcgt | caaagttgac | cgcgttggcg | atgctgcaaa | atcggcgct | 720 |
| ggcgcgaccc | gtatgaccac | taacccgcgc | gaactgctta | ttgcccgtag | cgctgcggat | 780 |
| gtgattgtca | actctggcta | cttcaaagaa | ggtttctcca | tgcaaaccgg | caccggcggc | 840 |
| gcatcgctgg | cggtaacccg | tttcctggaa | gacaaaatgc | gtagccgcga | tattcgcgcc | 900 |
| gacttcgccc | ttggcggtat | taccgcgacg | atggttgacc | tgcacgaaaa | aggtctgatc | 960 |
| cgcaaactgc | tggatgtgca | gagctttgac | agccatgctg | cgcaatcgct | ggcccgtaac | 1020 |
| cccaatcaca | tcgaaatcag | cgccaaccag | tacgctaact | gggttcgaa | aggcgcatcg | 1080 |
| gttgatcgtc | tcgacgtggt | ggtactgagc | gcgctggaaa | ttgacaccca | gttcaacgtt | 1140 |
| aacgtgctga | ccggctctga | cggcgtactg | cgtggtgctt | ccggtggtca | ctgcgatacc | 1200 |
| gcgattgcct | ctgcgctttc | catcatcgtc | gcgccgctgg | tacgcggtcg | tattccgact | 1260 |
| ctggtggata | acgtactgac | ctgcatcacc | ccaggctcca | gtgtcgatat | tctggtcaca | 1320 |

| | |
|---|---|
| gaccacggta tcgcagttaa cccggcacgt ccggaactgg cagaacgtct gcaggaagcg | 1380 |
| ggcattaaag tggttccat tgagtggctg cgcgaacgtg cgcgtctgct gaccggtgaa | 1440 |
| ccacagccga ttgaattcac agaccgcgtc gttgccgttg tgcgttaccg cgatggctcg | 1500 |
| gtgatcgatg ttgtgcatca ggtgaaggaa taa | 1533 |

<210> SEQ ID NO 24
<211> LENGTH: 909
<212> TYPE: DNA
<213> ORGANISM: Escherichia coli
<220> FEATURE:
<223> OTHER INFORMATION: Citryl CoA lyase; citE

<400> SEQUENCE: 24

| | |
|---|---|
| atgatttccg cttcgctgca acaacgtaaa actcgcaccc gccgcagcat gttgtttgtg | 60 |
| cctggtgcca atgccgcgat ggtcagcaac tccttcatct acccggctga tgccctgatg | 120 |
| tttgacctcg aagactccgt agcattgcgt gaaaaagaca ccgcccgccg catggtttac | 180 |
| cacgcgctgc aacatccgct gtatcgcgat attgaaacca ttgtgcgtgt caacgcgctg | 240 |
| gattccgaat ggggtgttaa cgacctggaa gccgtcgttc gcggtggtgc ggacgttgtg | 300 |
| cgtctgccga aaaccgatac cgctcaggat gttctgata ttgaaaaaga gatcctgcgt | 360 |
| atcgaaaaag cctgtggtcg tgaacccggc agcaccggcc tgctggcggc gattgaatct | 420 |
| ccgctgggga ttacccgcgc agtggaaatc gctcacgctt ccgagcgttt gatcggtatc | 480 |
| gccctcggtg cagaagacta tgtgcgcaac ctgcgtacag aacgctcccc ggaaggaact | 540 |
| gaactgctgt tcgcacgctg ttccattttg caggccgcgc gctctgcggg tattcaggcg | 600 |
| ttcgataccg tctattccga cgctaacaac gaagccggat ttctgcaaga agccgcccac | 660 |
| atcaaacagc tgggctttga cggcaaatcg ctgatcaacc cgcgtcagat tgatctgctg | 720 |
| cacaacctct acgcaccgac ccagaaagaa gtggatcacg cccgccgcgt cgtagaagcc | 780 |
| gctgaagccg ccgctcgcga aggcctcggc gtggtttccc tgaacggcaa gatggtggac | 840 |
| ggtccggtta tcgatcgcgc ccgtctggtg ctctcccgtg cagaactttc cggcatccgc | 900 |
| gaagaataa | 909 |

<210> SEQ ID NO 25
<211> LENGTH: 1167
<212> TYPE: DNA
<213> ORGANISM: Escherichia coli
<220> FEATURE:
<223> OTHER INFORMATION: Succinyl CoA synthetase; sucC

<400> SEQUENCE: 25

| | |
|---|---|
| atgaacttac atgaatatca ggcaaaacaa cttttttgccc gctatggctt accagcaccg | 60 |
| gtgggttatg cctgtactac tccgcgcgaa gcagaagaag ccgcttcaaa aatcggtgcc | 120 |
| ggtccgtggg tagtgaaatg tcaggttcac gctggtggcc gcggtaaagc gggcggtgtg | 180 |
| aaagttgtaa acagcaaaga agacatccgt gcttttgcag aaaactggct gggcaagcgt | 240 |
| ctggtaacgt atcaaacaga tgccaatggc caaccggtta accagattct ggttgaagca | 300 |
| gcgaccgata tcgctaaaga gctgtatctc ggtgccgttg ttgaccgtag ttcccgtcgt | 360 |
| gtggtcttta tggcctccac cgaaggcggc gtggaaatcg aaaaagtggc ggaagaaact | 420 |
| ccgcacctga tccataaagt tgcgcttgat ccgctgactg gcccgatgcc gtatcaggga | 480 |
| cgcgagctgg cgttcaaact gggtctgaa ggtaaactgg ttcagcagtt caccaaaatc | 540 |
| ttcatgggcc tggcgaccat tttcctggag cgcgacctgg cgttgatcga aatcaacccg | 600 |

```
ctggtcatca ccaaacaggg cgatctgatt tgcctcgacg gcaaactggg cgctgacggc    660
aacgcactgt tccgccagcc tgatctgcgc gaaatgcgtg accagtcgca ggaagatccg    720
cgtgaagcac aggctgcaca gtgggaactg aactacgttg cgctggacgg taacatcggt    780
tgtatggtta acgcgcaggt ctggcgatgg gtacgatggg acatcgttaa actgcacggc    840
ggcgaaccgg ctaacttcct tgacgttggc ggcggcgcaa ccaaagaacg tgtaaccgaa    900
gcgttcaaaa tcatcctctc tgacgacaaa gtgaaagccg ttctggttaa catcttcggc    960
ggtatcgttc gttgcgacct gatcgctgac ggtatcatcg gcgcggtagc agaagtgggt   1020
gttaacgtac cggtcgtggt acgtctggaa ggtaacaacg ccgaactcgg cgcgaagaaa   1080
ctggctgaca gcggcctgaa tattattgca gcaaaaggtc tgacggatgc agctcagcag   1140
gttgttgccg cagtggaggg gaaataa                                       1167

<210> SEQ ID NO 26
<211> LENGTH: 735
<212> TYPE: DNA
<213> ORGANISM: Escherichia coli
<220> FEATURE:
<223> OTHER INFORMATION: Fumarate Reductase; frdB

<400> SEQUENCE: 26
atggctgaga tgaaaaacct gaaaattgag gtggtgcgct ataacccgga agtcgatacc     60
gcaccgcata gcgcattcta tgaagtgcct tatgacgcaa ctacctcatt actggatgcg    120
ctgggctaca tcaaagacaa cctggcaccg gacctgagct accgctggtc ctgccgtatg    180
gcgatttgtg gttcctgcgg catgatggtt aacaacgtgc aaaactggc atgtaaaacc    240 ttcctgcgtg attacaccga cggtatgaag gttgaagcgt tagctaactt cccgattgaa    300
cgcgatctgg tggtcgatat gacccacttc atcgaaagtc tggaagcgat caaaccgtac    360
atcatcggca actcccgcac cgcggatcag ggtactaaca tccagacccc ggcgcagatg    420
gcgaagtatc accagttctc cggttgcatc aactgtggtt tgtgctacgc cgcgtgcccg    480
cagtttggcc tgaacccaga gttcatcggt ccggctgcca ttacgctggc gcatcgttat    540
aacgaagata gccgcgacca cggtaagaag gagcgtatgg cgcagttgaa cagccagaac    600
ggcgtatgga gctgtacttt cgtgggctac tgctccgaag tctgcccgaa acacgtcgat    660
ccggctgcgg ccattcagca gggcaaagta gaaagttcga agactttct tatcgcgacc    720 ctgaaaccac gctaa                                                    735

<210> SEQ ID NO 27
<211> LENGTH: 396
<212> TYPE: DNA
<213> ORGANISM: Escherichia coli
<220> FEATURE:
<223> OTHER INFORMATION: Fumarate Reductase; frdC

<400> SEQUENCE: 27
atgacgacta aacgtaaacc gtatgtacgg ccaatgacgt ccacctggtg gaaaaaattg     60
ccgttttatc gcttttacat gctgcgcgaa ggcacggcgg ttccggctgt gtggttcagc    120
attgaactga tttttcgggct gtttgccctg aaaaatggcc cggaagcctg gcgggattc    180 gtcgactttt tacaaaaccc ggttatcgtg atcattaacc tgatcactct ggcggcagct    240
ctgctgcaca ccaaaaacctg gtttgaactg gcaccgaaag cggccaatat cattgtaaaa    300
gacgaaaaaa tgggaccaga gccaattatc aaaagtctct gggcggtaac tgtggttgcc    360
```

```
accatcgtaa tcctgtttgt tgccctgtac tggtaa                              396
```

<210> SEQ ID NO 28
<211> LENGTH: 360
<212> TYPE: DNA
<213> ORGANISM: Escherichia coli
<220> FEATURE:
<223> OTHER INFORMATION: Fumarate Reductase; frdD

<400> SEQUENCE: 28

```
atgattaatc caaatccaaa gcgttctgac gaaccggtat tctggggcct cttcggggcc   60
ggtggtatgt ggagcgccat cattgcgccg gtgatgatcc tgctggtggg tattctgctg  120
ccactggggt tgtttccggg tgatgcgctg agctacgagc gcgttctggc gttcgcgcag  180
agcttcattg tcgcgtatt cctgttcctg atgatcgttc tgccgctgtg gtgtggttta  240
caccgtatgc accacgcgat gcacgatctg aaaatccacg tacctgcggg caaatgggtt  300
ttctacggtc tggctgctat cctgacagtt gtcacgctga ttggtgtcgt tacaatctaa  360
```

<210> SEQ ID NO 29
<211> LENGTH: 510
<212> TYPE: PRT
<213> ORGANISM: Escherichia coli
<220> FEATURE:
<223> OTHER INFORMATION: Citryl CoA lyase; citF

<400> SEQUENCE: 29

```
Met Thr Gln Lys Ile Glu Gln Ser Gln Arg Gln Glu Arg Val Ala Ala
1               5                   10                  15

Trp Asn Arg Arg Ala Glu Cys Asp Leu Ala Ala Phe Gln Asn Ser Pro
            20                  25                  30

Lys Gln Thr Tyr Gln Ala Glu Lys Ala Arg Asp Arg Lys Leu Cys Ala
        35                  40                  45

Asn Leu Glu Glu Ala Ile Arg Arg Ser Gly Leu Gln Asp Gly Met Thr
    50                  55                  60

Val Ser Phe His His Ala Phe Arg Gly Gly Asp Leu Thr Val Asn Met
65                  70                  75                  80

Val Met Asp Val Ile Ala Lys Met Gly Phe Lys Asn Leu Thr Leu Ala
                85                  90                  95

Ser Ser Ser Leu Ser Asp Cys His Ala Pro Leu Val Glu His Ile Arg
            100                 105                 110

Gln Gly Val Val Thr Arg Ile Tyr Thr Ser Gly Leu Arg Gly Pro Leu
        115                 120                 125

Ala Glu Glu Ile Ser Arg Gly Leu Leu Ala Glu Pro Val Gln Ile His
    130                 135                 140

Ser His Gly Gly Arg Val His Leu Val Gln Ser Gly Glu Leu Asn Ile
145                 150                 155                 160

Asp Val Ala Phe Leu Gly Val Pro Ser Cys Asp Glu Phe Gly Asn Ala
                165                 170                 175

Asn Gly Tyr Thr Gly Lys Ala Cys Cys Gly Ser Leu Gly Tyr Ala Ile
            180                 185                 190

Val Asp Ala Asp Asn Ala Lys Gln Val Val Met Leu Thr Glu Glu Leu
        195                 200                 205

Leu Pro Tyr Pro His Asn Pro Ala Ser Ile Glu Gln Asp Gln Val Asp
    210                 215                 220

Leu Ile Val Lys Val Asp Arg Val Gly Asp Ala Ala Lys Ile Gly Ala
225                 230                 235                 240
```

```
Gly Ala Thr Arg Met Thr Thr Asn Pro Arg Glu Leu Leu Ile Ala Arg
                245                 250                 255

Ser Ala Ala Asp Val Ile Val Asn Ser Gly Tyr Phe Lys Glu Gly Phe
            260                 265                 270

Ser Met Gln Thr Gly Thr Gly Gly Ala Ser Leu Ala Val Thr Arg Phe
        275                 280                 285

Leu Glu Asp Lys Met Arg Ser Arg Asp Ile Arg Ala Asp Phe Ala Leu
    290                 295                 300

Gly Gly Ile Thr Ala Thr Met Val Asp Leu His Glu Lys Gly Leu Ile
305                 310                 315                 320

Arg Lys Leu Leu Asp Val Gln Ser Phe Asp Ser His Ala Ala Gln Ser
                325                 330                 335

Leu Ala Arg Asn Pro Asn His Ile Glu Ile Ser Ala Asn Gln Tyr Ala
            340                 345                 350

Asn Trp Gly Ser Lys Gly Ala Ser Val Asp Arg Leu Asp Val Val Val
        355                 360                 365

Leu Ser Ala Leu Glu Ile Asp Thr Gln Phe Asn Val Asn Val Leu Thr
    370                 375                 380

Gly Ser Asp Gly Val Leu Arg Gly Ala Ser Gly Gly His Cys Asp Thr
385                 390                 395                 400

Ala Ile Ala Ser Ala Leu Ser Ile Ile Val Ala Pro Leu Val Arg Gly
                405                 410                 415

Arg Ile Pro Thr Leu Val Asp Asn Val Leu Thr Cys Ile Thr Pro Gly
            420                 425                 430

Ser Ser Val Asp Ile Leu Val Thr Asp His Gly Ile Ala Val Asn Pro
        435                 440                 445

Ala Arg Pro Glu Leu Ala Glu Arg Leu Gln Glu Ala Gly Ile Lys Val
    450                 455                 460

Val Ser Ile Glu Trp Leu Arg Glu Arg Ala Arg Leu Leu Thr Gly Glu
465                 470                 475                 480

Pro Gln Pro Ile Glu Phe Thr Asp Arg Val Val Ala Val Val Arg Tyr
                485                 490                 495

Arg Asp Gly Ser Val Ile Asp Val Val His Gln Val Lys Glu
            500                 505                 510

<210> SEQ ID NO 30
<211> LENGTH: 302
<212> TYPE: PRT
<213> ORGANISM: Escherichia coli
<220> FEATURE:
<223> OTHER INFORMATION: Citryl CoA lyase;citE

<400> SEQUENCE: 30

Met Ile Ser Ala Ser Leu Gln Gln Arg Lys Thr Arg Thr Arg Arg Ser
1               5                   10                  15

Met Leu Phe Val Pro Gly Ala Asn Ala Ala Met Val Ser Asn Ser Phe
            20                  25                  30

Ile Tyr Pro Ala Asp Ala Leu Met Phe Asp Leu Glu Asp Ser Val Ala
        35                  40                  45

Leu Arg Glu Lys Asp Thr Ala Arg Arg Met Val Tyr His Ala Leu Gln
    50                  55                  60

His Pro Leu Tyr Arg Asp Ile Glu Thr Ile Val Arg Val Asn Ala Leu
65                  70                  75                  80

Asp Ser Glu Trp Gly Val Asn Asp Leu Glu Ala Val Val Arg Gly Gly
                85                  90                  95
```

```
Ala Asp Val Val Arg Leu Pro Lys Thr Asp Thr Ala Gln Asp Val Leu
            100                 105                 110

Asp Ile Glu Lys Glu Ile Leu Arg Ile Glu Lys Ala Cys Gly Arg Glu
        115                 120                 125

Pro Gly Ser Thr Gly Leu Leu Ala Ala Ile Glu Ser Pro Leu Gly Ile
    130                 135                 140

Thr Arg Ala Val Glu Ile Ala His Ala Ser Glu Arg Leu Ile Gly Ile
145                 150                 155                 160

Ala Leu Gly Ala Glu Asp Tyr Val Arg Asn Leu Arg Thr Glu Arg Ser
                165                 170                 175

Pro Glu Gly Thr Glu Leu Leu Phe Ala Arg Cys Ser Ile Leu Gln Ala
            180                 185                 190

Ala Arg Ser Ala Gly Ile Gln Ala Phe Asp Thr Val Tyr Ser Asp Ala
        195                 200                 205

Asn Asn Glu Ala Gly Phe Leu Gln Glu Ala Ala His Ile Lys Gln Leu
    210                 215                 220

Gly Phe Asp Gly Lys Ser Leu Ile Asn Pro Arg Gln Ile Asp Leu Leu
225                 230                 235                 240

His Asn Leu Tyr Ala Pro Thr Gln Lys Glu Val Asp His Ala Arg Arg
                245                 250                 255

Val Val Glu Ala Ala Glu Ala Ala Arg Glu Gly Leu Gly Val Val
            260                 265                 270

Ser Leu Asn Gly Lys Met Val Asp Gly Pro Val Ile Asp Arg Ala Arg
        275                 280                 285

Leu Val Leu Ser Arg Ala Glu Leu Ser Gly Ile Arg Glu Glu
    290                 295                 300

<210> SEQ ID NO 31
<211> LENGTH: 388
<212> TYPE: PRT
<213> ORGANISM: Escherichia coli
<220> FEATURE:
<223> OTHER INFORMATION: Succinyl CoA synthetase; sucC

<400> SEQUENCE: 31

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
            20                  25                  30

Glu Ala Ala Ser Lys Ile Gly Ala Gly Pro Trp Val Val Lys Cys Gln
        35                  40                  45

Val His Ala Gly Gly Arg Gly Lys Ala Gly Gly Val Lys Val Val Asn
    50                  55                  60

Ser Lys Glu Asp Ile Arg Ala Phe Ala Glu Asn Trp Leu Gly Lys Arg
65                  70                  75                  80

Leu Val Thr Tyr Gln Thr Asp Ala Asn Gly Gln Pro Val Asn Gln Ile
                85                  90                  95

Leu Val Glu Ala Ala Thr Asp Ile Ala Lys Glu Leu Tyr Leu Gly Ala
            100                 105                 110

Val Val Asp Arg Ser Ser Arg Arg Val Val Phe Met Ala Ser Thr Glu
        115                 120                 125

Gly Gly Val Glu Ile Glu Lys Val Ala Glu Glu Thr Pro His Leu Ile
    130                 135                 140

His Lys Val Ala Leu Asp Pro Leu Thr Gly Pro Met Pro Tyr Gln Gly
145                 150                 155                 160
```

Arg Glu Leu Ala Phe Lys Leu Gly Leu Glu Gly Lys Leu Val Gln Gln
               165                 170                 175

Phe Thr Lys Ile Phe Met Gly Leu Ala Thr Ile Phe Leu Glu Arg Asp
           180                 185                 190

Leu Ala Leu Ile Glu Ile Asn Pro Leu Val Ile Thr Lys Gln Gly Asp
       195                 200                 205

Leu Ile Cys Leu Asp Gly Lys Leu Gly Ala Asp Gly Asn Ala Leu Phe
   210                 215                 220

Arg Gln Pro Asp Leu Arg Glu Met Arg Asp Gln Ser Gln Glu Asp Pro
225                 230                 235                 240

Arg Glu Ala Gln Ala Ala Gln Trp Glu Leu Asn Tyr Val Ala Leu Asp
               245                 250                 255

Gly Asn Ile Gly Cys Met Val Asn Gly Ala Gly Leu Ala Met Gly Thr
           260                 265                 270

Met Asp Ile Val Lys Leu His Gly Gly Glu Pro Ala Asn Phe Leu Asp
       275                 280                 285

Val Gly Gly Gly Ala Thr Lys Glu Arg Val Thr Glu Ala Phe Lys Ile
   290                 295                 300

Ile Leu Ser Asp Asp Lys Val Lys Ala Val Leu Val Asn Ile Phe Gly
305                 310                 315                 320

Gly Ile Val Arg Cys Asp Leu Ile Ala Asp Gly Ile Ile Gly Ala Val
               325                 330                 335

Ala Glu Val Gly Val Asn Val Pro Val Val Arg Leu Glu Gly Asn
           340                 345                 350

Asn Ala Glu Leu Gly Ala Lys Lys Leu Ala Asp Ser Gly Leu Asn Ile
       355                 360                 365

Ile Ala Ala Lys Gly Leu Thr Asp Ala Ala Gln Gln Val Val Ala Ala
   370                 375                 380

Val Glu Gly Lys
385

<210> SEQ ID NO 32
<211> LENGTH: 244
<212> TYPE: PRT
<213> ORGANISM: Escherichia coli
<220> FEATURE:
<223> OTHER INFORMATION: Fumarate Reductase; FrdB

<400> SEQUENCE: 32

Met Ala Glu Met Lys Asn Leu Lys Ile Glu Val Val Arg Tyr Asn Pro
1               5                   10                  15

Glu Val Asp Thr Ala Pro His Ser Ala Phe Tyr Glu Val Pro Tyr Asp
            20                  25                  30

Ala Thr Thr Ser Leu Leu Asp Ala Leu Gly Tyr Ile Lys Asp Asn Leu
        35                  40                  45

Ala Pro Asp Leu Ser Tyr Arg Trp Ser Cys Arg Met Ala Ile Cys Gly
    50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
        115                 120                 125

```
Asp Gln Gly Thr Asn Ile Gln Thr Pro Ala Gln Met Ala Lys Tyr His
    130                 135                 140
Gln Phe Ser Gly Cys Ile Asn Cys Gly Leu Cys Tyr Ala Ala Cys Pro
145                 150                 155                 160
Gln Phe Gly Leu Asn Pro Glu Phe Ile Gly Pro Ala Ala Ile Thr Leu
                165                 170                 175
Ala His Arg Tyr Asn Glu Asp Ser Arg Asp His Gly Lys Lys Glu Arg
                180                 185                 190
Met Ala Gln Leu Asn Ser Gln Asn Gly Val Trp Ser Cys Thr Phe Val
            195                 200                 205
Gly Tyr Cys Ser Glu Val Cys Pro Lys His Val Asp Pro Ala Ala Ala
    210                 215                 220
Ile Gln Gln Gly Lys Val Glu Ser Ser Lys Asp Phe Leu Ile Ala Thr
225                 230                 235                 240
Leu Lys Pro Arg
```

<210> SEQ ID NO 33
<211> LENGTH: 131
<212> TYPE: PRT
<213> ORGANISM: Escherichia coli
<220> FEATURE:
<223> OTHER INFORMATION: Fumarate Reductase; FrdC

<400> SEQUENCE: 33

```
Met Thr Thr Lys Arg Lys Pro Tyr Val Arg Pro Met Thr Ser Thr Trp
1               5                   10                  15
Trp Lys Lys Leu Pro Phe Tyr Arg Phe Tyr Met Leu Arg Glu Gly Thr
            20                  25                  30
Ala Val Pro Ala Val Trp Phe Ser Ile Glu Leu Ile Phe Gly Leu Phe
        35                  40                  45
Ala Leu Lys Asn Gly Pro Glu Ala Trp Ala Gly Phe Val Asp Phe Leu
    50                  55                  60
Gln Asn Pro Val Ile Val Ile Ile Asn Leu Ile Thr Leu Ala Ala Ala
65                  70                  75                  80
Leu Leu His Thr Lys Thr Trp Phe Glu Leu Ala Pro Lys Ala Ala Asn
                85                  90                  95
Ile Ile Val Lys Asp Glu Lys Met Gly Pro Glu Pro Ile Ile Lys Ser
                100                 105                 110
Leu Trp Ala Val Thr Val Val Ala Thr Ile Val Ile Leu Phe Val Ala
            115                 120                 125
Leu Tyr Trp
    130
```

<210> SEQ ID NO 34
<211> LENGTH: 119
<212> TYPE: PRT
<213> ORGANISM: Escherichia coli
<220> FEATURE:
<223> OTHER INFORMATION: Fumarate Reductase; FrdD

<400> SEQUENCE: 34

```
Met Ile Asn Pro Asn Pro Lys Arg Ser Asp Glu Pro Val Phe Trp Gly
1               5                   10                  15
Leu Phe Gly Ala Gly Gly Met Trp Ser Ala Ile Ile Ala Pro Val Met
            20                  25                  30
Ile Leu Leu Val Gly Ile Leu Leu Pro Leu Gly Leu Phe Pro Gly Asp
        35                  40                  45
```

-continued

```
Ala Leu Ser Tyr Glu Arg Val Leu Ala Phe Ala Gln Ser Phe Ile Gly
     50                  55                  60

Arg Val Phe Leu Phe Leu Met Ile Val Leu Pro Leu Trp Cys Gly Leu
65              70                  75                      80

His Arg Met His His Ala Met His Asp Leu Lys Ile His Val Pro Ala
                85                  90                  95

Gly Lys Trp Val Phe Tyr Gly Leu Ala Ala Ile Leu Thr Val Val Thr
             100                 105                 110

Leu Ile Gly Val Val Thr Ile
         115
```

RECOMBINANT METHANOTROPHIC BACTERIUM AND A METHOD OF PRODUCTION OF SUCCINIC ACID FROM METHANE OR BIOGAS THEREOF

CROSS-REFERENCE TO RELATED APPLICATIONS

The present application is a U.S. National Phase Application of International Patent Application No. PCT/IN2015/000169, filed Apr. 13, 2015, which claims priority to Indian Patent Application No. 1910/CHE/2014, filed Apr. 11, 2014, the entireties of which are incorporated herein by reference.

SEQUENCE LISTING

The instant application contains a Sequence Listing which has been submitted electronically in ASCII format and is hereby incorporated by reference in its entirety. Said ASCII copy, created on Dec. 5, 2016, is named 056859-0276_SL.txt and is 94,797 bytes in size.

FIELD OF THE INVENTION

The present invention relates to the field of waste management, and more particularly relates to converting organic waste to succinic acid by employing recombinant methanotrophic bacteria.

BACKGROUND OF THE INVENTION

As global living standards and urban populations continue to rise, there's a concurrent increase in the amount of waste generated. Waste management has become the single largest expenditure for most municipalities. Ineffective management of waste is posing serious risk of rapid deterioration in levels of sanitation and general quality of urban life.

Disposal of wastes is commonly done by dumping (on land or into water bodies), incineration, and/or long term storage in a secured facility. All these methods have varying degrees of negative environmental impacts with adverse health risks if not properly executed. Apart from these methods, recycling, composting, recovery (including resource and energy), and biological reprocessing etc. are emerging as acceptable sustainable modes of waste management. In recycling, materials generally undergo a chemical transformation and resultant products are recycled to be used for various purposes. For the purpose of resource recovery the organic waste is preferably anaerobically digested (also called Anaerobic Composting or Biomethanation) as compared to aerobic digestion to obtain compost which can be used as an organic fertilizer on agricultural fields. Anaerobic digestion of organic waste results in energy in the form of biogas, and compost in the form of a liquid residual. The biogas consists of methane and carbon dioxide and can be used as fuel or, by using a generator, it can be converted to electricity on-site. This reduces greenhouse gas emissions by using methane as an energy source which would otherwise be emitted from landfilling waste. Landfilling waste gas is similar in composition to biogas with lower amount of methane and differences in component gases. However, the conversion of biogas to electricity is not economically attractive and also results in significant loss of energy during conversion.

Methane, present in biogas or landfill gas, can also be converted to syngas and then to chemicals such as methanol. This gas to liquid conversion happens at high temperature and pressure necessitating huge capital investments.

Efficient utilization of biogas as well as methane has always been a challenging task. Advances in biotechnology are enabling development of new and improved microorganisms for efficient conversion of biomass to useful products. However, the existing state of the art does not provide for a unified and efficient way of converting organic wastes and more specifically biogas or methane to target chemicals by employing recombinant microorganisms.

SUMMARY OF THE INVENTION

The present disclosure provides recombinant methanotrophic bacterium for converting organic waste to succinic acid It further provides methods for using the recombinant methanotrophic bacterium for converting biogas or methane (produced by anaerobic digestion of the organic waste) to succinic acid. The present invention successfully solves the problems in converting organic waste to a useful chemical thereby providing an environment-friendly and commercially viable solution for waste management.

In one aspect of the present invention, a recombinant methanotrophic bacterium for producing succinic acid from biogas or methane is provided. The said recombinant methanotrophic bacterium includes exogenous nucleic acid(s) or gene(s) encoding for a first group of enzymes consisting of malate dehydrogenase, pyruvate carboxylase, phosphoenol pyruvate carboxylase, phosphofructokinase, citryl-CoA lyase, isocitrate lyase, fumarate reductase, malate synthase, aspartate transaminase, succinyl CoA synthetase, pyruvate kinase or any combination thereof.

In further aspect of the present invention, increasing production of succinic acid in the recombinant methanotrophic bacterium from biogas or methane is provided by overexpression or/and down-regulation of selected gene(s).

In another aspect of the present invention, a process of producing succinic acid using the recombinant methanotrophic bacterium is provided. The process comprises the steps of receiving biogas and/or methane as input, culturing the bacterium in the input thereby converting the input into succinic acid, and optionally purifying or separating the succinic acid produced from the culture for obtaining the succinic acid.

In yet another aspect of the present invention, a process of producing succinic acid using recombinant methanotrophic bacterium is provided. The process comprises the steps of receiving organic waste as an input, anaerobically digesting the organic waste to biogas, culturing the bacterium in the biogas so generated thereby converting the biogas to the succinic acid and optionally purifying the succinic acid produced from the culture for obtaining the succinic acid. During the second step of culturing the recombinant methanotrophic bacterium in the biogas following parameters were maintained: temperature ranging from about 35° C. to about 50° C., preferably 45° C., pH ranging from about 4 to about 7, preferably 5.8, and dissolved oxygen concentration of <20%.

In a further aspect of the present invention, the process of producing succinic acid using recombinant methanotrophic bacterium further comprises cleaning the generated biogas to remove carbon dioxide and other impurities present in the biogas so as to obtain methane. The recombinant methanotrophic bacteria are cultured in the methane so obtained.

Other features of the embodiments will be apparent from the accompanying drawings and from the detailed description that follows.

BRIEF DESCRIPTION OF THE ACCOMPANYING DRAWINGS

Figure 3:
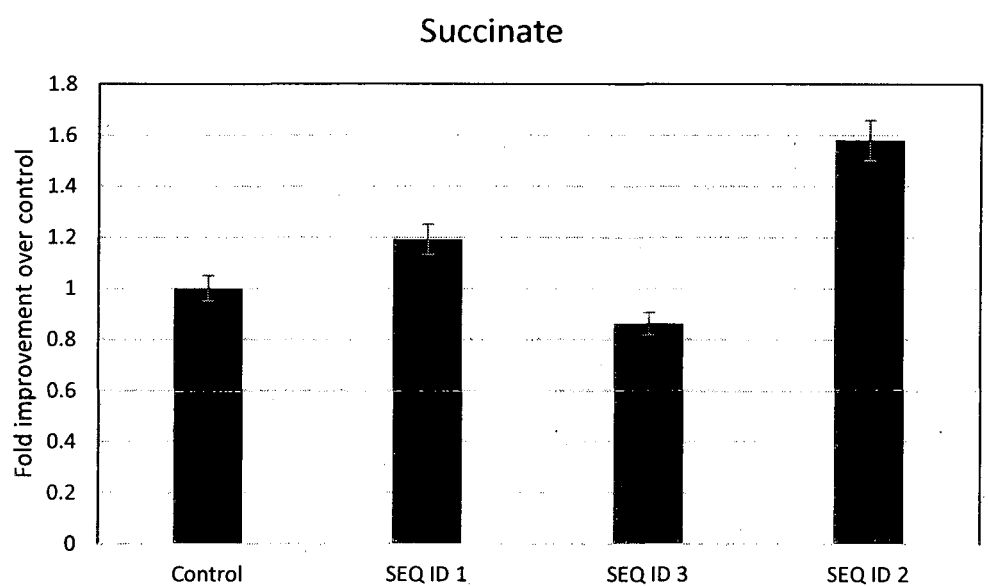

FIG. 3 is a graph illustrating the comparison between recombinant and wildtype *M. capsulatus* grown in culture tubes according to one embodiment. Genes overexpressed from pSB107 (SEQ ID 1), pSB108 (SEQ ID 2), pSB109 (SEQ ID 3) in *M. capsulatus* were tested for succinic acid production. Some recombinant strains had higher levels of succinic acid compared to control strain.

Figure 4:
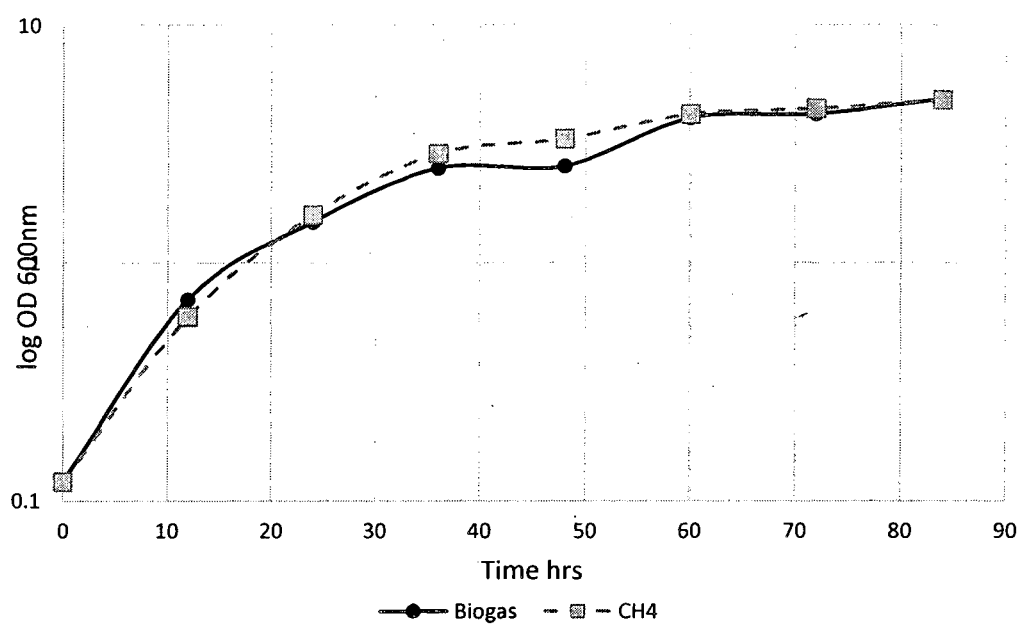

FIG. 4 is a graph depicting comparative growth profile of methanotroph strain on Biogas and Methane.

Figure 5:
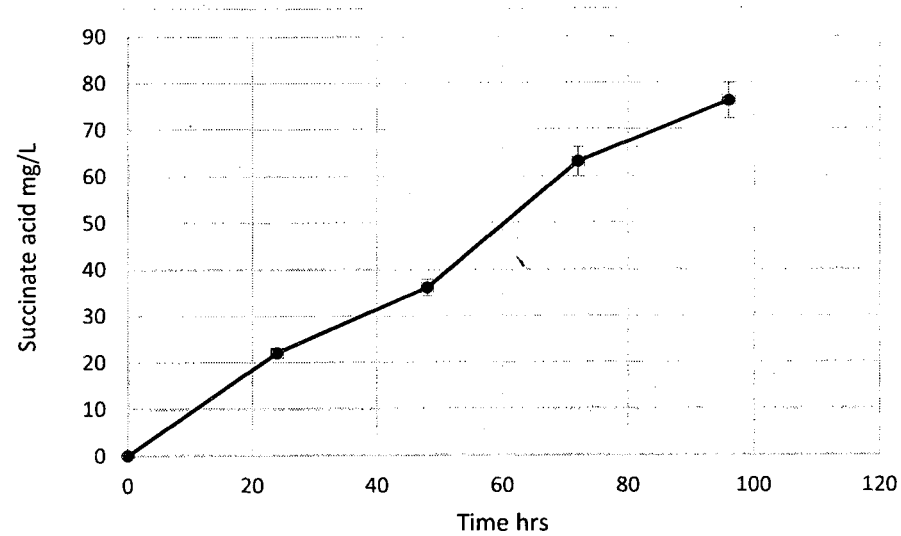

FIG. 5 is a graph highlighting increase in succinic acid production as a function of time, wherein the conversion of biogas, generated from organic waste, to succinic acid is performed using recombinant methanotroph strain no with over-expressed malate dehydrogenase (SEQ ID 1; pSB107), according to one embodiment.

Figure 6:
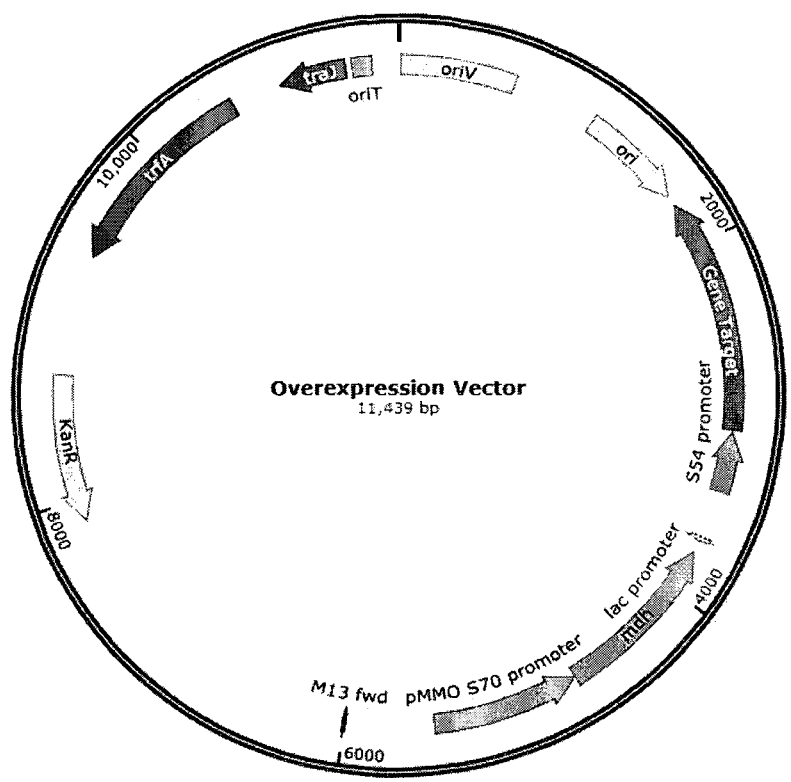

FIG. 6 illustrates a plasmid map of a vector for cloning and expression of overexpression gene targets under the control of a σ54 promoter, according to one embodiment.

Figure 7:
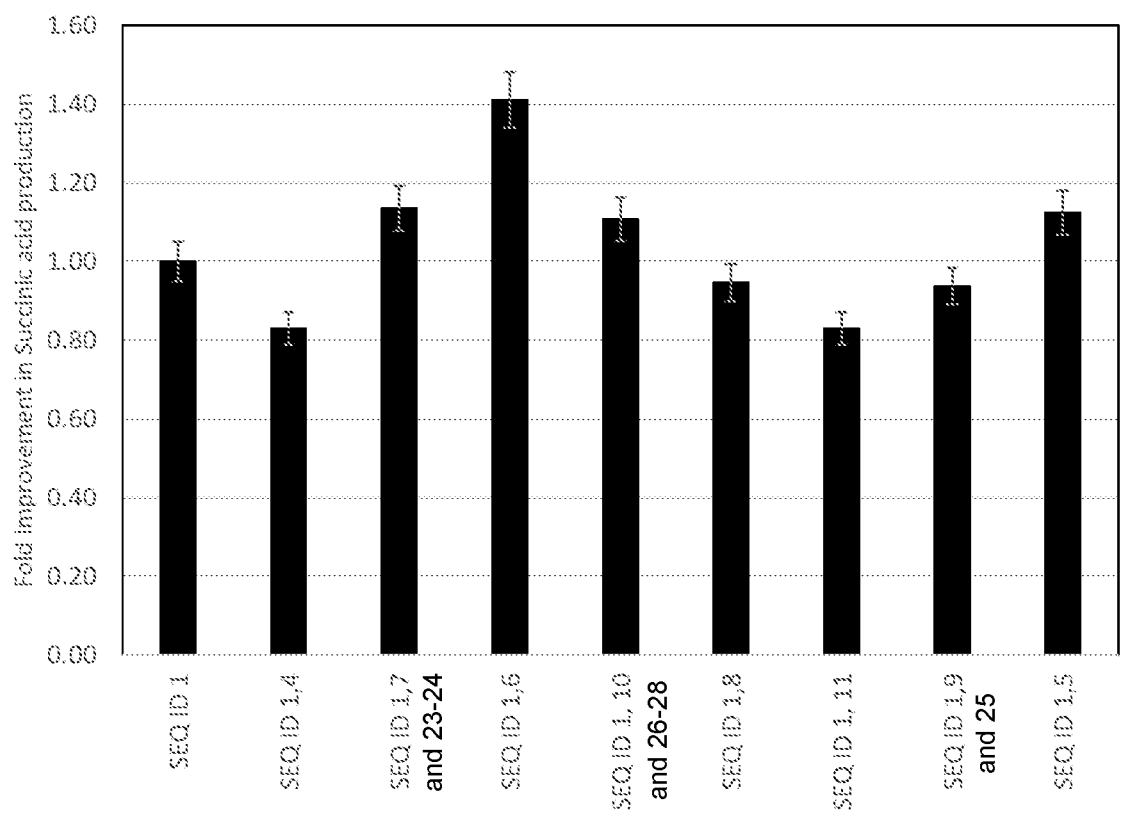

FIG. 7 is a graph depicting effect of the overexpression of various gene combinations on succinic acid production in the recombinant *M. capsulatus*, according to one embodiment. The genes encode for Malate dehydrogenase, Phosphofructokinase, Pyruvate Kinase, Isocitrate Lyase, Citryl CoA Lyase (D, F, E subunits) Malate synthase A, Succinyl CoA Synthetase (C, D subunits), Fumarate Reductase (A, B, C, D subunits).

DEPOSIT OF MICROORGANISM

The following microorganism has been deposited in accordance with the terms of the Budapest Treaty with the Microbial Type Culture Collection and Gene Bank (MTCC), Chandigarh, India:

| Identification ref. | Taxonomic designation | MTCC Accession number |
|---|---|---|
| STB18 | *Methylococcus capsulatus* | MTCC 25005 |

The recombinant *Methylococcus capsulatus* capable of converting methane to succinic acid was deposited as MTCC Accession No.: MTCC 25005 on Jan. 27, 2015 with the Microbial Type Culture Collection and Gene Bank (MTCC), Institute of Microbial Technology, Sector 39-A, Chandigarh—160036, INDIA. The MTCC issued an accession number in this matter on Mar. 26, 2015. STB18 refers to the recombinant *M. capsulatus* strain with the gene corresponding to SEQ ID 1 overexpressed from pSB107 plasmid. This deposit was made under the provisions of the Budapest Treaty on the International Recognition of the Deposit of Microorganisms for the Purposes of Patent Procedure and the Regulations thereunder (Budapest Treaty). Availability of the deposited strain is not to be construed as a license to practice the invention in contravention of the rights granted under the authority of any government in accordance with its patent laws.

DETAILED DESCRIPTION OF THE INVENTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with and techniques of biochemistry, enzymology, molecular and cellular biology, microbiology, genetics and protein/nucleic acid chemistry and hybridization described herein are those well-known and commonly used in the art. Certain references and other documents cited herein are expressly incorporated herein by reference. In case of conflict, the present specification, including definitions, will control. The materials, methods, and examples are illustrative only and not intended to be limiting.

Before the present vectors, genomes, bacteria, microbes, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing," and is inclusive or open-ended and does not exclude additional, unrecited members, elements or method steps.

The term "polynucleotide", "nucleic acid molecule", "nucleic acid", or "nucleic acid sequence" refers to a polymeric form of nucleotides of at least 10 bases in length. The term includes DNA molecules and RNA molecules, as well as analogs of DNA or RNA containing non-natural nucleotide analogs, non-native internucleoside bonds, or both. The nucleic acid can be in any topological conformation.

The term "protein" or "polypeptide" as used herein indicates a polymeric form of amino acids composed of two or more amino acidic monomers and/or analogs thereof. As used herein, the term "amino acid" or "amino acidic monomer" refers to any natural and/or synthetic amino acids.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "Heterologous" or "exogenous" refers to molecules, specifically polynucleotides or polypeptides or enzymes that are not present naturally in the host or that is native to the host but at altered expression levels when compared to natural expression levels. These are expressed independently at levels of expression higher, equal or lower than the level of expression in a native organism.

As used herein, nucleic acid construct, nucleic acid (e.g., a polynucleotide), polypeptide, or host cell is referred to as "recombinant" when it is non-naturally occurring, artificial or engineered. In some embodiments, recombinant constructs contain two or more naturally-occurring sequences that are linked together in a way that does not occur naturally. A recombinant cell contains a recombinant polynucleotide. For clarity, reference to a cell of a particular strain refers to a parental cell of the strain as well as progeny and genetically modified derivatives of the same.

As used herein, "vector" refers to a nucleic acid molecule capable of transporting another nucleic acid to which it has been linked into a cell.

The terms "percent identity", "percent identical", "% identical" and "% identity" are used interchangeably herein to refer to the percent amino acid or polynucleotide sequence identity that is obtained by ClustalW2 analysis (EMBL—EBI, Cambridge, UK), counting the number of identical matches in the alignment and dividing such number of identical matches by the length of the reference sequence, and using the following ClustalW2 parameters to achieve slow/accurate pairwise optimal alignments—DNA/Protein Gap no Open Penalty:15/10; DNA/Protein Gap Extension Penalty:6.66/0.1; Protein weight matrix: Gonnet series; DNA weight matrix: Identity; Toggle Slow/Fast pairwise alignments=SLOW or FULL Alignment; DNA/Protein Number of K-tuple matches:2/1; DNA/Protein number of best diagonals: 4/5; DNA/Protein Window size:4/5.

The term "methanotrophs" or "methanotrophic bacteria" herein refers to bacteria that utilize methane as a source of carbon and energy. These bacteria are widely present in nature and can be found in areas of high methane content such as oceans, mud, marshes, underground environments, soils, rice paddies and landfills. Some of these are obligate and can only use methane as a source of carbon and energy. Some of these are facultative and are known to additionally use other substrates such as succinate, acetate, pyruvate etc.

The term "organic waste" herein refers to the components of waste that can be broken down into its base components in a reasonable amount of time by microorganisms. Organic waste can be found in commonly occurring sources of waste such as municipal solid waste, green waste, food waste, paper waste, biodegradable waste, human waste, sewage, manure and slaughterhouse waste.

The term "Anaerobic digestion" herein refers to a set of processes wherein several types of microorganisms break down biodegradable material in the absence of oxygen. The end products are a gas containing mostly methane and carbon dioxide, referred to as biogas, and a slurry or solid fraction, referred to as digestate. Different technologies are available for anaerobic digestion that vary in the process and process parameters affecting digestion.

The term "biogas" herein refers to the major product resulting from anaerobic digestion of waste. Typical composition of biogas is methane (50-75%), carbon dioxide (25-50%), nitrogen (0-10%), hydrogen (0-1%), hydrogen Sulphide (0-3%), oxygen (0-2%) and water vapour (3-5%). The biogas composition can vary depending on, among other factors, the type of waste, its organic matter load, feeding rate of digester and conditions of anaerobic digestion. Biogas is typically lighter than air and produces less calories by combustion compared to equal volume of natural gas. Biogas is typically used for heating, generating electricity or as cooking fuel.

As used herein the phrase "biogas cleaning" or "biogas upgrading" or "biogas scrubbing" refers to the process of removing the non-methane components of biogas. Depending on the use of the biogas, the extent of biogas cleaning can vary. Different methods of cleaning the various non-methane components of biogas are known and practiced. Hydrogen Sulphide can be removed by among others biological fixation by using iron oxidizing bacteria, dosing with iron chloride, water scrubbing, absorption activated carbon or bubbling through sodium hydroxide. Water vapor present in biogas can be removed by among others passive cooling, refrigeration, absorption into a drying medium, or adsorption into silica gel. Ammonia present in the biogas is usually in very low amounts and can be removed by water scrubbing. Oxygen and nitrogen are typically not present in large amounts in biogas and can be removed by adsorption with activated carbon, molecular sieves or membranes. "Biogas upgrading" more typically refers to the removal of carbon dioxide from the biogas to increase the energy content of the gas. Some technologies for removing carbon dioxide are commercially available and some are at the pilot or demo scale. Pressure swing adsorption is a process wherein the carbon dioxide can be removed by adsorption onto materials like activated carbon or zeolites under elevated pressure. Another method is removal of carbon dioxide by absorption. This is usually done by a counter current flow of biogas with a liquid in a column filled with plastic packaging. Absorption can be done using water, organic solvents or amine solutions. Another classical method used is membrane separation using materials that are permeable to carbon dioxide, water and ammonia.

The terms "succinic acid" and "succinate" are used interchangeably in the context of the invention.

The present invention provides an environment-friendly and commercially viable way of handling waste by converting the organic waste into useful chemicals, namely succinic acid, by employing the recombinant methanotrophic bacteria capable of converting methane or biogas into succinic acid.

In one of the embodiments, the present invention provides for a recombinant methanotrophic bacterium capable of producing succinic acid from biogas or methane. The recombinant methanotrophic bacterium produces higher amounts of succinic acid as compared to wildtype methanotrophic bacterium when fed with biogas or methane. Further, most importantly the recombinant methanotrophic bacterium accumulates the succinic acid so produced. The methanotrophs in ordinary course do not accumulate succinate as it serves as a native intermediate for central carbon metabolism.

Figure 1:
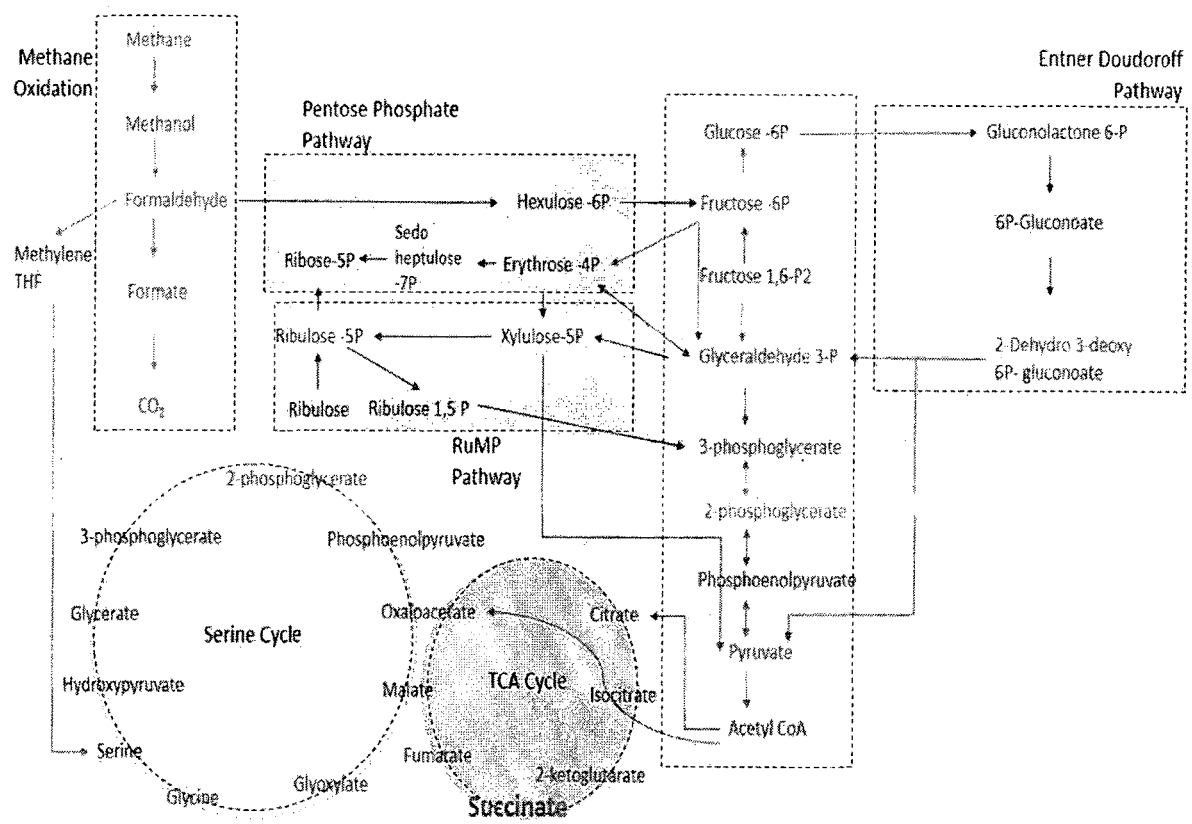
FIG. 1 illustrates some aspects of methanotroph metabolism and a pathway for conversion of methane to succinate in *M. capsulatus*, according to one embodiment.

Methanotrophs or methanotrophic bacteria are unique in their ability to utilize methane as a sole carbon and energy source. However, the methanotrophs are not well established industrial hosts. They are present in a wide variety of environments and play a critical role in the oxidation of methane in the natural world (Hanson, R. S., & Hanson, T. E. (1996). Methanotrophic bacteria. *Microbiological Reviews*, 60(2), 439-471). The methanotrophs are classified into two major groups based on the pathways used for assimilation of formaldehyde, the major source of cell carbon, and other physiological and morphological features. Type I methanotrophs employ the RuMP pathway for formaldehyde assimilation, whereas type II methanotrophs employ the serine pathway for formaldehyde assimilation. The use of enzymes known as methane monooxygenases MMOs (EC 1.14.13.25) to catalyze the oxidation of methane to methanol is a defining characteristic of methanotrophs. The oxidation of methane by aerobic methanotrophs is initiated by MMOs utilizing two reducing equivalents to split the O—O bonds of dioxygen. One of the oxygen atoms is reduced to form $H_2O$, and the other is incorporated into methane to form $CH_3OH$ methanol. Two forms of MMOs have been found in methanotrophic bacteria, a soluble form (sMMO) and a membrane bound form, pMMO. Methanol is oxidized to formaldehyde by methanol dehydrogenase (MDH), an enzyme that's highly expressed in most methanotrophs. The further oxidation of formaldehyde to carbon dioxide via formate provides most of the reducing power required for the oxidation of methane. Multiple enzymes are known that catalyze the oxidation of formaldehyde to formate. The further oxidation of formate to carbon dioxide is catalyzed by an NAD-dependent formate dehydrogenase. Formaldehyde produced from the oxidation of methane and methanol by methanotrophic bacteria is assimilated to form intermediates of the central metabolic routes that are subsequently used for biosynthesis of cell material. The two known pathways used by methanotrophic bacteria for the synthesis of multicarbon compounds from formaldehyde are the serine pathway, in which 2 mol of formaldehyde and 1 mol of carbon dioxide are utilized to form a three-carbon intermediate, and the RuMP cycle for the assimilation of 3 mol of formaldehyde to form a three-carbon intermediate of central metabolism (FIG. 1).

In one of the embodiments, the recombinant microorganism of the present invention is selected from a group of organisms comprising: *Methylococcus capsulatus, Methylomicrobium album, Methylocapsa acidiphila, Methylocella silvestris, Methylosinus trichosporium, Methylacidiphilum infernorum V4, Methylomonas methanica, Methylosinus sporium, Methylocella palustris, Methylocystis parvus, Methylovulum miyakonense, Methylocystis echinoides, Methylomonas rubra, Methylococcus thermophilus, Methylomonas aurantiaca, Methylomonas fodinarum, Methylomicrobium japanense*, and, *Methylococcaceae* bacterium.

Some species of methanotrophs including, but not limited to, *Methylococcus capsulatus, Methylocella silvestris*, etc. are well-characterized and basic molecular biology tools for host manipulation have been developed.

In an exemplary embodiment, the recombinant methanotrophic bacterium for producing succinic acid is created from *Methylococcus capsulatus*.

In another exemplary embodiment, the recombinant methanotrophic bacterium for producing succinic acid is created from *Methylococcus capsulatus* (Bath).

In yet another embodiment, the recombinant methanotrophic bacterium for producing succinic acid is created from *Methylococcus trichosporium*.

In various embodiments of the recombinant methanotrophic bacterium, the present invention provides multiple ways of increasing the succinic acid production including:

(a) overexpression of one or more genes encoding for certain key enzymes of TCA cycle;

(b) overexpression of one or more genes encoding for certain key enzymes of central carbon metabolism;

(c) overexpression of one or more genes encoding for enzymes of methane metabolism;

(d) overexpression of one or more genes encoding for non-native enzymes;

(e) overexpression of one or more genes encoding for transporters;

(f) deletion or downregulation of genes encoding for enzymes of the central carbon metabolism/TCA cycle; and (g) deletion or downregulation of genes encoding for enzymes used by pathways that compete with succinate production.

It is to be noted that (a) to (g) could be used independently or in any combination thereof.

Expression of the heterologous genes may be accomplished by conventional molecular biology means (Green. M. R. & Sambrook. J, *Molecular Cloning—A laboratory Manual*, Fourth Edition). For example, the heterologous genes can be under the control of an inducible promoter or a constitutive promoter. The heterologous genes may either be integrated into a chromosome of the host microorganism, or exist as an extra-chromosomal genetic elements that can be stably passed on ("inherited") to daughter cells. Such extra-chromosomal genetic elements (such as plasmids, BAC, YAC, etc.) may additionally contain selection markers that ensure the presence of such genetic elements in daughter cells.

As used herein, the term "overexpress" is intended to encompass increasing the expression or activity of a gene or protein to a level greater than the cell normally produces. It is intended that the term encompass overexpression of endogenous, as well as heterologous gene or proteins. Overexpression of genes or proteins can be done by conventional molecular biology methods. In some embodiments, the genes can be overexpressed by introducing additional copies of the genes on the chromosome or extra-chromosomally on plasmids, BACs or YACs. In certain embodiments, the expression can be increased by optimizing the nucleotide sequence for expression in the specific host such as through codon optimization. In other embodiments, the gene expression can be increased by altering the promoter or ribosome binding site operably linked to the gene. In yet other embodiments the gene activity can be increased through mutations in the gene that enhance the enzymatic activity.

The term "down-regulated" or "deleted" used herein with reference to a gene or protein, indicates any modification in the genome and/or proteome of a microorganism that eliminates or reduces the biological activity of the gene, protein or enzyme either directly or indirectly. For example, deletion or downregulation of gene or protein can be performed by deleting or mutating a native or heterologous polynucleotide encoding for the gene or protein in the microorganism, by deleting or mutating a native or heterologous polynucleotide encoding for an enzyme involved in the pathway for the synthesis of the gene or protein in the microorganism, by activating a further native or heterologous molecule that inhibits the expression of the gene or protein in the microorganism. In particular, in some embodiments inactivation of a gene or protein such as an enzyme can be performed by deleting from the genome of the recombinant microorganism one or more endogenous genes encoding for the enzyme.

For assembly of the constructs to enable overexpression or downregulation or deletion of specific gene, conventional molecular biology methods can be used (Green, M. R. and Sambrook, J, 2001). *Molecular cloning: a laboratory manual*. Cold Spring Harbor, N.Y.: Cold Spring Harbor Laboratory; Ellis, T., Adie, T., & Baldwin, G. S. (2011); *DNA assembly for synthetic biology: from parts to pathways and beyond. Integrative Biology: Quantitative Biosciences from Nano to Macro*, 3(2), 109-18).

Assembly of DNA parts through restriction digestion and ligation is well-established and known to those skilled in the art. Other methods that offer standardized, scarless, sequence independent, multi piece DNA assembly such as SLIC (Sequence and Ligation Independent Cloning), Gibson assembly, CPEC (Circular Polymerase Extension Cloning) or SLiCE (Sequence and Ligation Cloning Extract) have more recently been established. In some embodiments, SLIC based assembly is used for generating DNA constructs or vectors for overexpression or downregulation or deletion. In other embodiments CPEC is used for assembly of DNA constructs for overexpression, deletion or down-regulation. In further embodiments, methods such as site-directed mutagenesis, transposon mutagenesis, crispr/cas assisted genome engineering and recombineering can be used directly for overexpression, down-regulation or deletion of specific gene or protein.

In one embodiment of the recombinant methanotrophic bacterium, increase in succinate production is achieved by overexpressing the genes coding for enzymes of TCA cycle such as, but not limited to, fumarase (fumC/B/A), malate dehydrogenase (mdh), malate:quinone oxidoreductase (mqo), isocitrate dehydrogenase (icd), 2-oxoglutarate dehydrogenase (sucA/B), 2-oxoglutarate dehydrogenase (lpd), citryl-CoA lyase, isocitrate lyase, malate synthase, fumarate reductase and succinyl-CoA synthetase (suc C/D).

In another embodiment of the recombinant methanotrophic bacterium, increase in succinate production is achieved by overexpression of genes encoding for keys enzymes of central carbon metabolism such as, but not limited to, pyruvate dehydrogenase, pyruvate kinase, phosphoenol pyruvate carboxylase, hexulose 6-phosphate (hps) synthase, 6-phospho-3-hexuloisomerase, phosphor-fructo kinase, fructose-bisphosphate aldolase, transketolase, transaldolase, ribulose-5 phosphate epimerase, pyruvate carboxylase, aspartate transaminase and phosphoenolpyruvate carboxykinase.

In yet another embodiment of the recombinant methanotrophic bacterium, increase in succinate production is achieved by overexpression of genes encoding for enzymes of methane metabolism such as, but not limited to, methane monooxygenase and methanol dehydrogenase.

In yet another embodiment of the recombinant methanotrophic bacterium, increase in succinate production is achieved by overexpression of genes encoding for non-native enzymes such as, but not limited to, succinate transporters and dehydrogenases.

In a further embodiment of the recombinant methanotrophic bacterium, increase in succinate production is achieved by overexpression of gene encoding for transporters such as, but not limited to, *Schizosaccharomyces pombe* malate transporter gene SpMAE1 and *E. coli* C4 dicarboxylic/orotate symporter dctA.

Table 1 enlists sources of the exogenic genes along with their Seq ID NOs. (encoding for the enzymes) selected for overexpression in the methanotrophic bacterium in various embodiments of the present invention.

TABLE 1

| SEQ ID NO: | Gene | Host |
|---|---|---|
| SEQID 1 | Malate dehydrogenase | E.coli |
| SEQ ID 2 | Pyruvate carboxylase | P.aeruginosa |
| SEQ ID 3 | Phosphoenol pyruvate carboxylase | E.coli |
| SEQ ID 4 | Phosphofructokinase | M. capsulatus Bath |
| SEQ ID 5 | Pyruvate Kinase | E.coli |
| SEQ ID 6 | Isocitrate Lyase | E.coli |
| SEQ ID NOS 7, 23 & 24, respectively | Citryl CoA Lyase (D, F, E subunits) | E.coli |
| SEQ ID 8 | Malate synthase A | E.coli |
| SEQ ID NOS 25 & 9, respectively | Succinyl CoA Synthetase (C, D subunits) | E.coli |
| SEQ ID NOS 10, 26, 27, & 28, respectively | Fumarate Reductase (A, B, C, D subunits) | E.coli |
| SEQ ID 11 | Aspartate transaminase | E.coli |

The enzymes enlisted in Table 1, having gene sequence ID Nos: 1 to 11 and 23 to 28, code for amino acid sequences that are at least 80% identical to reference amino acid sequence set forth in SEQ ID Nos: 12 to 22 and 29 to 34.

Table 2 provides a list of genes encoding for the enzymes and its respective amino acid sequence.

TABLE 2

| Enzyme | Gene SEQ ID NO | Amino Acid SEQ ID NO |
|---|---|---|
| Malate dehydrogenase | SEQ ID 1 | SEQ ID 12 |
| Pyruvate carboxylase | SEQ ID 2 | SEQ ID 13 |
| Phosphoenol pyruvate carboxylase | SEQ ID 3 | SEQ ID 14 |
| Phosphofructokinase | SEQ ID 4 | SEQ ID 15 |
| Pyruvate Kinase | SEQ ID 5 | SEQ ID 16 |
| Isocitrate Lyase | SEQ ID 6 | SEQ ID 17 |
| Citryl CoA Lyase (D, F, E subunits) | SEQ ID NOS 7, 23 & 24, respectively | SEQ ID NOS 18, 29 & 30, respectively |
| Malate synthase A | SEQ ID 8 | SEQ ID 19 |
| Succinyl CoA Synthetase (C, D subunits) | SEQ ID NOS 25 & 9, respectively | SEQ ID NOS 31 & 20, respectively |
| Fumarate Reductase (A, B, C, D subunits) | SEQ ID NOS 10, 26, 27 & 28, respectively | SEQ ID NOS 21, 32, 33 & 34, respectively |
| Aspartate transaminase | SEQ ID 11 | SEQ ID 22 |

In another embodiment of the recombinant methanotrophic bacterium, increase in succinate production is achieved by deletion or downregulation of gene(s) encoding for enzyme(s) of the central carbon metabolism/TCA cycle or gene(s) encoding for enzymes used by pathways that compete with succinate production such as, but not limited to, glucose-6-phosphate dehydrogenase, succinate dehydrogenase, pyruvate decarboxylase, malate:quinone oxidoreductase, citrate synthase, isocitrate dehydrogenase, lactate dehydrogenase, acetyl CoA synthase, phosphotransacetylase, formaldehyde dehydrogenase and formate dehydrogenase.

The present invention also provides for a method of creating the recombinant methanotrophic bacterium that converts methane to succinic acid at an efficient rate while accumulating the same. In one embodiment, the method of creating the recombinant *Methylococcus capsulatus* strain includes:

(a) the genes/operons encoding for enzymes, used in the succinate pathway, Malate dehydrogenase (mdh), Fumarase (fumA/fumB/fumC), Fumarate reductase (frdA/frdB/frdC/frdD) were amplified and cloned into a shuttle vector; and (b) the vector is transformed into *M. capsulatus* and positive transformants of *M. capsulatus* containing the genes/operons encoding for enzymes Malate dehydrogenase (mdh), Fumarase (fumA/fumB/fumC), Fumarate reductase (frdA/frdB/frdC/frdD) were verified by PCR.

Thereafter, the recombinant *M. capsulatus* is grown using standard methods in the presence of methane or biogas. The recombinant methanotrophs so created when fed with methane not only produces greater amount of succinic acid as compared to natural occurring *M. capsulatus* but also accumulates the succinic acid so produced.

In one exemplary embodiment, Malate dehydrogenase (mdh *E. coli*; SEQ ID 1), pyruvate carboxylase (pyc *P. aeruginosa*, SEQ ID 2), phospho enol pyruvate carboxylase (pepc *E. coli*, SEQ ID 3), genes were amplified individually from genomic DNA using primers flanked with SacI and SphI/PciI restriction enzymes. The amplified gene/operon was restriction digested with SacI and SphI/PciI and cloned into the same sites in the broad host range vector pMHA201 to create pSB107, pSB108, and pSB109. pMHA201 (Alit, H., & Murrell, J. C., *Development and validation of promoter-probe vectors for the study of methane monooxygenase gene expression in Methylococcus capsulatus* Bath, Microbiology, 155(3), pp. 761-771 (2009)) is a plasmid with a broad range Origin of replication (OriV), Kanamycin resistance gene, Ampicillin resistance gene and OriT for conjugative transfer. Plasmid pSB107, pSB108 and pSB109 were sequence verified.

Methanotroph strains were cultivated in nitrate mineral salt (NMS) medium. NMS agar plates were prepared with 1.5% (w/v) Bacto agar. Antibiotics were added as required: Kanamycin (30 μg/ml) and Gentamicin (5 μg/ml). Methanotrophs were typically grown in 250 ml conical flasks with 24/29 joint containing 50 ml NMS medium. Flasks were sealed with suba-seals and gassed with 50 ml (i.e. ~20%) methane/carbon dioxide (95/5, v/v mix). Methanotrophs grown on NMS agar plates were incubated in gas-tight container under a methane/air/carbon dioxide atmosphere (50/45/5, by vol.) at the appropriate temperature. The gas was replenished every 2 days until colonies formed, usually within 5-10 days. *M. capsulatus* Bath. (From Prof. Colin Murrell, University of Norwich) derived strains were incubated at 45° C. Conjugation of pSB107, pSB108 and pSB109 into *M. capsulatus* was done based on the protocol described by Martin, H., & Murrell, J. C. (1995), *Methane monooxygenase mutants of Methylosinus trichosporium constructed by marker-exchange mutagenesis*, FEMS Microbiology Letters, 127(3), 243-248. 30 mL of *M. capsulatus* culture was spun down and resuspended in 5 mL of NMS media. 2 mL of *E. coli* S.17 lambda pir bearing the plasmid to be conjugated was spun down, washed with 1 mL of NMS and resuspended again in 1 mL of NMS. The two cultures were mixed and filtered onto a 0.2μ nitrocellulose membrane. The membrane was placed on an NMS agar plate containing 0.02% (w/v) proteose peptone and incubated for a duration of 24 hours at 37° C. in a gas-tight container under a methane/air/carbon dioxide atmosphere (50/45/5, by vol.). Following incubation, the cells were washed with 1 ml NMS and collected by centrifugation (7,000×g for 5 minutes). Aliquots (50-100 μl) of the cells were spread onto NMS plates containing 30 μg/ml kanamycin for plasmid selection and incubated at 45° C. in a gas-tight container under a methane/air/carbon dioxide atmosphere (50/45/5, by vol.). Colonies typically formed on the plates after 8-12 days. Colonies were re-streaked onto NMS agar plates with 30 ug/ml of kanamycin to confirm the true recombinant strains.

Recombinant methanotrophic strains with SEQ ID 1 had >10% improved levels of succinic acid compared to control. Recombinant methanotrophic strains with SEQ ID 2 had >50% improved levels of succinic acid when compared to control.

Recombinant strains that had combinations of genes overexpressed had further improvements in levels of succinic acid compared to recombinant strains with single gene overexpression. Recombinant strain with SEQ ID 1 and 6 had >40% improved levels of succinic acid compared to recombinant strains with a single gene overexpression.

The present invention also provides a process for organic waste management by using the recombinant methanotrophic bacterium capable of producing succinic acid from biogas or methane. The process broadly involves (a) converting the waste to biogas by anaerobic digestion, (b) converting biogas to succinic acid by using the recombinant methanotrophic bacterium, or alternatively scrubbing the biogas so produced to have methane and then converting it to succinic acid by using the recombinant methanotrophic bacterium.

In one embodiment, biogas is used as an input for producing succinic acid by employing the recombinant methanotrophic bacterium. The process steps include:

A. Anaerobically digesting organic waste to break it down to biogas via three distinct stages of hydrolysis, acetogenesis, and methanogenesis. In the first stage, a group of microorganisms comprising fermentative bacteria, secreting enzymes (lipases, proteases, cellulases, amylases, etc.), hydrolyses polymeric materials to monomers such as sugars and amino acids. In the next stage, products of the first stage are subsequently converted by a second group of bacteria comprising acetogenic bacteria to simple organic acids, carbon dioxide and hydrogen. In the final stage, a third group of bacteria comprising methanogens converts carbon dioxide, hydrogen and acetate to methane. Various aspects of the process of breaking down of solid waste have been well-researched, stream lined, and solutions at various scales have been developed. The most valuable component of biogas is methane ($CH_4$) which constitutes around 50-60%, the remaining portion comprises carbon dioxide ($CO_2$) and small percentages of other gases. The overall process of anaerobic digestion and output varies depending on the size of plant, type of waste, process conditions for fermentation, type of fermentation process etc.

B. Cleaning up the biogas to remove carbon dioxide and other impurities present in the gas. The cleaning further includes two steps—(i) cleaning of hydrogen sulphide ($H_2S$), $NH_3$, water vapour and other impurities, and (ii) removal of carbon dioxide. Methods employed for biogas purification include, but not limited to, chemical absorption, high pressure water scrubbing, pressure swing adsorption, cryogenic separation, and membrane separation. The steps employed are well-researched and optimised to achieve efficient purification. The main output from this process is the methane gas.

C. Third step of the process plays most significant part where the methane gas is converted to succinic acid by using the recombinant methanotrophic bacterium capable of metabolising methane/biogas to produce succinic acid. The process of converting methane to succinic acid includes:

(1) Conversion of methane to methanol involves oxidation of methane to methanol by the methane monooxygenase enzyme (EC number EC 1.14.13.25). As mentioned above the methane monooxygenases (MMOs) are unique enzymes that can catalyze the oxidation of methane in the presence of oxygen;

(2) Conversion of methanol to formaldehyde involves oxidation of methanol to formaldehyde by methanol dehydrogenase (EC 1.1.1.244). Gram negative methanotrophs have a periplasmic methanotroph that is cytochrome c dependent. Gram positive methanotrophs have a NAD dependent enzyme that catalyzes this step;

(3) Conversion of formaldehyde to pyruvate via central carbon metabolism involving assimilation of formaldehyde into central carbon metabolism of the methanotrophs and conversion to pyruvate via the steps of the RuMP pathway or serine pathway. Formaldehyde is a key intermediate that gets assimilated into the central carbon metabolism;
(4) Conversion of pyruvate into acetyl CoA by components of pyruvate dehydrogenase complex (EC 1.2.4.1); and
(5) Conversion of acetyl CoA into succinate via enzymes of the tricarboxylic acid cycle.

The pathway for succinate production in some instances encompasses carbon dioxide fixation. One mole of carbon dioxide is incorporated into phosphoenol pyruvate to make oxaloacetetate catalyzed by phosphoenol pyruvate carboxylase. In addition, malic enzyme and pyruvate carboxylase incorporate one mole of carbon dioxide into pyruvate to form malate and oxaloacetate, respectively. Oxaloacetate or malate is then converted to succinic acid by enzymes of the TCA cycle.

In an alternate embodiment, biogas is directly used as input without cleaning it up to remove carbon dioxide and other impurities, hence omitting the step B provided for the above described embodiment, for producing succinic acid.

In another alternate embodiment, the biogas used as the input has varying ratios of methane to carbon dioxide such as, but not limited to, from 95% methane:5% $CO_2$ to 50% methane:50% $CO_2$. Depending on the type of substrates used, anaerobic digestion, biogas cleaning etc. the ratio of methane to carbon dioxide in the input may vary. In some embodiments the ratio of methane to carbon dioxide is 95%:5%. In other embodiments it can be 50% methane:50% carbon dioxide. In another alternate embodiment, the biogas used as the input has varying ratios of methane to carbon dioxide such as, but not limited to, from 95% methane:5% $CO_2$ to 50% methane:50% $CO_2$.

In yet another embodiment, purified methane gas is used as an input for producing succinic acid by employing the recombinant methanotrophic bacterium. The process of converting methane to succinic acid includes:
(1) Conversion of methane to methanol involves oxidation of methane to methanol by the methane monooxygenase enzyme (EC number EC 1.14.13.25). As mentioned above the methane monooxygenases (MMOs) are unique enzymes that can catalyze the oxidation of methane in the presence of oxygen;
(2) Conversion of methanol to formaldehyde involves oxidation of methanol to formaldehyde by methanol dehydrogenase (EC 1.1.1.244). Gram negative methanotrophs have a periplasmic methanotroph that is cytochrome c dependent. Gram positive methanotrophs have a NAD dependent enzyme that catalyzes this step;
(3) Conversion of formaldehyde to pyruvate via central carbon metabolism involving assimilation of formaldehyde into central carbon metabolism of the methanotrophs and conversion to pyruvate via the steps of the RuMP pathway or serine pathway. Formaldehyde is a key intermediate that gets assimilated into the central carbon metabolism;
(4) Conversion of pyruvate into acetyl CoA by components of pyruvate dehydrogenase complex (EC 1.2.4.1); and
(5) Conversion of acetyl CoA into succinate via enzymes of the tricarboxylic acid cycle.

In another embodiment, efficiency of succinate production and accumulation is increased by overexpressing enzymes involved in carbon dioxide fixation such as, but not limited to, pyruvate carboxylase, phosphoenol pyruvate carboxylase, malic enzyme, and phosphoenolpyruvate carboxykinase etc.

The conditions of fermentation of the biogas or methane to succinic acid also directly affects the production of succinic acid. Some of the key parameters affecting the fermentation of biogas are conditions such as pH, temperature, dissolved oxygen concentration in the media, composition of the media etc. Some of the conditions are optimized for the recombinant menthanotroph for optimal production of succinic acid. In one embodiment, preferred temperature for fermentation is the optimal temperature for growth of *M. capsulatus*, i.e. 45° C. In other embodiments, the temperature for fermentation may vary from 35° C. to 50° C. In another embodiment, the pH during fermentation is maintained at the pH which is optimal for the strain, i.e. pH 5.8. In other embodiments, the pH during fermentation is maintained at pH lower than 6.8. In a further embodiment, the pH is maintained from about 3 to about 7. In yet another embodiment, the pH is maintained from about 4 to about 6. Another parameter that has a critical effect on the succinic acid production is the dissolved oxygen concentration in the media. In some instances this is maintained at 20% of maximum DO. In another embodiment, the DO is maintained at <20% DO.

Succinic acid has been traditionally used as following: a surfactant—an additive, as a detergent and foaming agent; an ion chelator—for preventing the corrosion and spot corrosion of metal in the electroplating industry; an acidulant—a pH regulator and flavoring agent in the food industry; pharmaceutical products—including the production of antibiotics, amino acids, and vitamins (Zeikus et al. 1999).

Recently, succinic acid is getting a lot of attention for production of biodegradable polymers. Succinic acid and its derivative diamines and diols can be used as monomer units of a variety of plastics, such as polyesters, polyamides, and polyester amides (Bechthold et al. 2008). Among them, poly(butylene succinate) (PBS) and its copolymers are a family of biodegradable polyesters synthesised from succinic acid. The PBS owing to its excellent thermal processability, balanced mechanical properties, and good biodegradability can be used as a suitable substitute for conventional plastics. The PBS can be used to prepare supermarket bags, packaging film, mulch film, and other disposable articles.

Succinic acid produced from organic waste can be more cost-effective than the fossil-based processes. The present invention is further making the situation better by providing the recombinant methanotrophic bacterium capable of converting methane or biogas to succinic acid at an efficient rate.

The present invention provides a cradle to cradle solution for managing organic waste. The organic waste is anaerobically digested to produce biogas and compost. The resultant biogas is further efficiently converted to succinic acid by employing the recombinant methanotrophic bacterium. At present, succinic acid can be made commercially by hydrogenation of fossil-derived maleic acid (anhydride). However, non-renewability and the rising price of the fossil resources have limited the use of succinic acid. Hence, the present invention not only produces succinic acid from waste at a cost effective rate but also reduces the greenhouse emission by effectively utilising methane forming a major part of biogas. The target chemical succinic acid is an excellent building block for manufacturing variety of commercially viable products including, but not limited to, biodegradable polymers. The biodegradable polyester synthesised from succinic acid is PBS which owing to its properties of excellent thermal processability, balanced mechanical properties, and good biodegradability make it an appropriate substitute for conventional plastics. The PBS can be used for industrial packaging, wrapping, milk sachets, foodservice, personal care, pharmaceuticals, surgical implants, medical devices, recreation, etc. These products can be reused to make the input methane or biogas stream once the lifecycle of these products is completed. The increase in production and re-use of biodegradable plastic will effectively solve disposability problem associated with the use of conventional plastics, since the waste biodegradable plastics do not create environmental hazard and can be converted to target chemicals which may be used again to produce useful products. This can effectively contribute to the ongoing efforts of ensuring sustainability in environment.

EXAMPLES

The present invention is explained further in the following specific examples which are only by way of illustration and are not to be construed as limiting the scope of the invention.

Example 1: Cloning Succinate Pathway Genes into a Shuttle Vector

Figure 2:
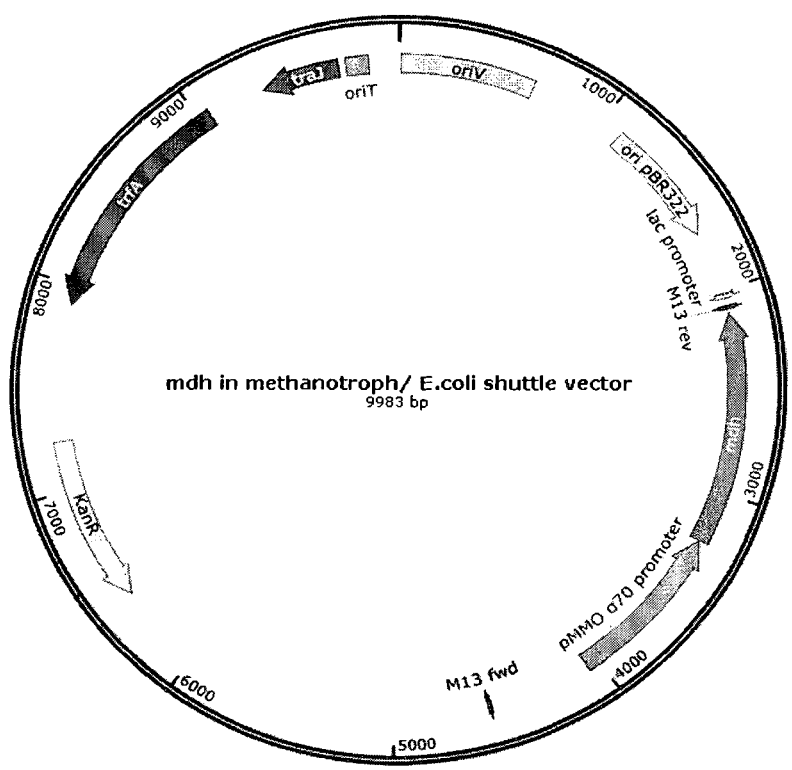
FIG. 2 illustrates a plasmid map of malate dehydrogenase cloned in a bacterial shuttle vector, where malate dehydrogenase from *E. coli* (mdh) was PCR amplified and cloned under a 70 promoter in a methanotroph/*E. coli* shuttle vector, according to one embodiment.

Malate dehydrogenase (mdh *E. coli*; SEQ ID 1), pyruvate carboxylase (pyc *P. aeruginosa* (MTCC 424), SEQ ID 2), phospho enol pyruvate carboxylase (pepc *E. coli*, SEQ ID 3), genes were amplified individually from genomic DNA using primers flanked with SacI and SphI/PciI restriction enzymes. The amplified gene/operon was restriction digested and cloned into the same sites in the broad host range vector pMHA201 to create pSB107 (FIG. 2), pSB108, and pSB109. pMHA201 (Alit, H., & Murrell, J. C, *Development and validation of promoter-probe vectors for the study of methane monooxygenase gene expression in Methylococcus capsulatus* Bath, Microbiology, 155(3), pp 761-771. (2009)) is a plasmid with a broad range Origin of replication (OriV), Kanamycin resistance gene, Ampicillin resistance gene and OriT for conjugative transfer. Plasmid pSB107, pSB108 and pSB109 were sequence verified.

Example 2: Transformation of Succinate Pathway Genes into Methanotrophs

Methanotrophs were cultivated in nitrate mineral salt (NMS) medium. NMS medium was prepared. NMS agar plates were prepared with 1.5% (w/v) Bacto agar. Antibiotics were added as required: kanamycin (30 µg/ml) and Gentamicin (5 µg/ml).

Methanotrophs were typically grown in 250 ml conical flasks with 24/29 joint containing 50 ml NMS medium. Flasks were sealed with suba-seals (Sigma Aldrich, Cat Num: Z279773-10EA) and gassed with 50 ml (i.e. ~20%) methane/carbon dioxide (95/5, v/v mix). *M. capsulatus* Bath (from Prof. Colin Murrell, University of Norwich) derived strains were incubated at 45° C. with shaking at 200 rpm. *M. trichosporium* (from Prof. Colin Murrell, University of Norwich) derived strains were incubated at 30° C. A typical methanotrophic culture took about 4-6 days to reach stationary phase. Methanotrophs grown on NMS agar plates were incubated in gas-tight container under a methane/air/carbon dioxide atmosphere (50/45/5, by vol.) at the appropriate temperature. The gas was replenished every 2 days until colonies formed, usually within 5-10 days depending on the strain.

Conjugation of pSB107, pSB108, pSB109 individually into *M. capsulatus* was done based on the protocol described by individually into *M. capsulatus* was done based on the protocol described by Martin, H., & Murrell, J. C. (1995), *Methane monooxygenase mutants of Methylosinus trichosporium constructed by marker-exchange mutagenesis*, FEMS Microbiology Letters, 127(3), 243-248. 30 mL of methanotroph culture was spun down and resuspended in 5 mL of NMS. 2 mL of *E. coli* S.17 lambda pir (Strand, T. A., Lale, R., Degnes, K. F., Lando, M., & Valla, S., *A New and Improved Host-Independent Plasmid System for RK2-Based Conjugal Transfer. PLoS ONE*, 9(3), (2014)) bearing the plasmid to be conjugated was spun down, washed with 1 mL of NMS and resuspended again in 1 mL of NMS. The two cultures were mixed and filtered onto a 0.2µ nitrocellulose membrane. The membrane was placed on an NMS agar plate containing 0.02% (w/v) proteose peptone and incubated for a duration of 24 hours at 37° C.

Following incubation, the cells were washed with 1 ml NMS and collected by centrifugation (7,000×g for 5 minutes). Aliquots (50-100 µl) of the cells were spread onto NMS plates containing 30 µg/ml kanamycin for plasmid selection and incubated at 45° C. in a gas-tight container under a methane/air/carbon dioxide atmosphere (50/45/5, by vol.). Colonies typically formed on the plates after 8-12 days. Colonies were re-streaked onto NMS agar plates with 30 ug/ml of kanamycin to confirm the true transformants.

Example 3: Growth and Assay of Methane to Succinate Activity

Positive transformants of *M. capsulatus* containing the malate dehydrogenase (mdh; SEQ ID 1; pSB107), pyruvate carboxylase (pyc; SEQ ID 2, pSB108), phospho enol pyruvate carboxylase (ppc; SEQ ID 3, pSB109) genes were verified by PCR. These were inoculated into 5 ml of liquid NMS media taken in 30 ml culture tubes and sealed with suba seals. 15 ml of Methane mixture (95% CH4; 5% CO2) was introduced into the culture tube using a syringe. The tubes were incubated at 45° C. at 250 rpm agitation. Once the culture OD reached 1, the cultures was centrifuged and the supernatant samples were taken and assayed for succinic acid. The organic acid concentrations were measured using Succinic Acid assay kit (Megazyme International; K-SUCC) according to manufacturer's protocol (FIG. 3).

Some of the recombinant strains had higher levels of succinic acid compared to the control strain. Recombinant strain with SEQ ID 1 was >15% improved when compared to the native strain. Recombinant strain with SEQ ID 2 was >50% improved when compared to the native strain.

Example 4: Growth of Methanotroph Strains on Biogas Generated from Organic Waste Methanotroph strain *Methylococcus capsulatus* was grown on methane and biogas in parallel to test the effect of biogas constituents on growth. Biogas used for this analysis was from an anaerobic digester that processes kitchen waste. Food waste was anaerobically digested using BioOrja biomethanation reactor (GPS Renewables, Bangalore). Bioorja generates 70 kg of LPG equivalent from 1 ton of food waste. The composition of the biogas was largely 60-65% $CH_4$; 35-30% $CO_2$; Traces—$H_2S$; Traces—$NH_3$. For methane, a commercial mixture of 95% $CH_4$: 5% $CO_2$ was used. Nitrate mineral salts medium was used for strain growth. Methanotroph strain, *M. capsulatus*, was inoculated into 5 ml of NMS media taken in 30 ml culture tubes. The tubes were sealed with suba seals. 15 ml of methane or biogas was fed into the tubes using a syringe. The tubes were incubated at 45° C. at 250 rpm agitation. Samples were taken from the tubes every 24 hrs and cell growth was measured by monitoring OD at 600 nm. When growth was compared for *M. capsulatus* between biogas and methane, the growth profile of the strain on biogas was similar to the growth profile on commercial methane mixture (FIG. 4).

Example 5: Growth and Assay of Biogas to Succinic Acid Fermentation

Recombinant *Methylococcus capsulatus* with malate dehydrogenase gene cloned in a broad host range vector (SEQ ID 1, pSB107) was grown in biogas and tested for conversion of biogas to succinic acid. Biogas used for this analysis was obtained from kitchen waste digested using the BioOrja reactor. The composition of the biogas was largely 60-65% $CH_4$; 35-30% $CO_2$; Traces—$H_2S$; Traces—$NH_3$. Recombinant strain and control were inoculated in 5 ml of NMS media containing 30 ug/ml of Kanamycin taken in 30 ml culture tubes. The culture tubes were sealed with suba seals. 15 ml of biogas was fed into the culture tubes using a syringe. The cells were growth in conditions optimal for growth: 45° C. and 200 rpm. 0.5 ml samples were taken at every 24 hrs and measured for OD and succinic acid levels. The samples were centrifuged and the supernatant was assayed for succinic acid using the Succinic acid assay kit (Megazyme International; K-SUCC) according to manufacturer's protocol. FIG. 5 shows the results for production of succinic acid from biogas. Succinic acid levels in the strain increase with time.

These studies were done with biogas without upgrading the biogas to remove carbon dioxide. Alternately, the biogas can be cleaned up to remove the carbon dioxide by having a basic purification unit in place. Water scrubbing is a basic method used to remove the carbon dioxide. Pressurized biogas is fed to the bottom of a packed column where water is fed on the top and the absorption process is operated counter-currently. The cleaned up gas with >90% of methane can be used for growth of strains and succinic acid production.

Examples 6: Effect of Gene(s) Over Expression on Methane to Succinic Acid Production To improve the levels of succinate production via gene overexpression, specific gene(s) were targeted for overexpression in *Methylococcus capsulatus*. Table 3 enlists genes cloned into vector pSB107 and tested for overexpression.

TABLE 3

| Sl. No. | Gene | Host Organism | Size of cloned fragment | SEQ ID NO |
|---|---|---|---|---|
| 1 | 6-Phosphofructokinase | *M. capsulatus* Bath | 1,263 bp | SEQ ID 4 |
| 2 | Pyruvate Kinase | *E.coli* | 1,467 bp | SEQ ID 5 |
| 3 | Isocitrate Lyase | *E.coli* | 1,305 bp | SEQ ID 6 |
| 4 | Citryl CoA Lyase | *E.coli* | 2,745 bp | SEQ ID NOS 7, 23 & 24, respectively |
| 5 | Malate synthase A | *E.coli* | 1,602 bp | SEQ ID 8 |
| 6 | Succinyl CoA Synthetase | *E.coli* | 2,036 bp | SEQ ID NOS 25 & 9, respectively |
| 7 | Fumarate Reductase | *E.coli* | 3,312 bp | SEQ ID NOS 10, 26, 27 & 28, respectively |
| 8 | Aspartate transaminase | *E.coli* | 1,191 bp | SEQ ID 11 |

In order to clone the genes into pSB107, σ54 promoter was cloned into pSB107 using Sequence and Ligation Independent Cloning (SLIC). Above genes were amplified with a 20 bp overlap to the above base vector and introduced under the σ54 promoter using SLIC (FIG. 6). SLIC was done in a 10 µl reaction according to the following set up: 50-100 ng of vector; 200-400 ng of insert; 1× Buffer 2.1 (NEB); 0.3 ul of T4 DNA Polymerase. All components except the enzyme was added and kept on ice for 5 minutes. The enzyme was added to the mixture, mixed well and incubated on ice for 10 minutes. 4 µl of the reaction mixture was transformed into *E. coli* and selected on LB/Kan plates to select for true transformants. True transformants were confirmed by PCR.

Vectors were purified from *E. coli* and conjugated into *M. capsulatus* based on the protocol described by Martin & Murrell 1995 and elaborated above. True conjugants were selected on NMS agar plates with 30 µg/ml of Kanamycin.

To test the effect of overexpression on succinic acid production, recombinant strains and control were inoculated in 5 ml of NMS media containing 30 µg/ml of Kanamycin taken in 30 ml culture tubes. The culture tubes were sealed with suba seals. 15 ml of methane was fed into the culture tubes using a syringe. The cells were growth in conditions optimal for growth: 45° C. and 200 rpm. Samples were taken at 72 hours and measured for OD and succinic acid levels. The samples were centrifuged and the supernatant was assayed for succinic acid using the Succinic acid assay kit (Megazyme International; K-SUCC) according to manufacturer's protocol.

Specific combinations of genes had a positive effect on succinic acid production when compared to the recombinant strain with a single gene overexpression. The comparative analysis/assessment of various combinations of genes is depicted in FIG. 7. It is evident that some of the combinations of genes are showing better results in terms of fold improvement in succinic acid production, such as SEQ ID 1,6>SEQ ID 1, 7, 23 & 24>SEQ ID 1,5>SEQ ID 1, 10, 26, 27 & 28 and so on.

While the invention has been described in detail with reference to preferred embodiments thereof, it will be apparent to one skilled in the art that various changes can be made, and equivalents employed, without departing from the scope of the invention.

The invention claimed is:

1. A recombinant *Methylococcus capsulatus* bacterium for producing succinic acid from organic waste, biogas or methane, comprising:
one or more exogenous nucleic acids or genes encoding a first group of enzymes selected from
malate dehydrogenase, pyruvate carboxylase, phosphoenol pyruvate carboxylase, citryl-CoA lyase, isocitrate lyase, fumarate reductase, malate synthase, aspartate transaminase, succinyl CoA synthetase, pyruvate kinase, and combinations thereof.

2. The recombinant *Methylococcus capsulatus* bacterium as claimed in claim 1, wherein the recombinant *Methylococcus capsulatus* bacterium produces higher amounts of succinic acid as compared to the corresponding wildtype *Methylococcus capsulatus* bacterium lacking the one or more exogenous nucleic acids or genes and accumulates the succinic acid so produced when cultured in the presence of methane or biogas.

3. The recombinant *Methylococcus capsulatus* bacterium as claimed in claim 1, wherein the one or more exogenous nucleic acids or genes encoding the first group of enzymes are selected from the group consisting of the polynucleotides of SEQ ID NO. 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO:11.

4. The recombinant *Methylococcus capsulatus* bacterium as claimed in claim 1, wherein the one or more exogenous nucleic acids or genes encoding for the first group of enzymes are from microorganisms selected from the group consisting of *E. coli, P. aeruginosa, Methylosinus trichosporium, Methylococcus capsulatus* and *Schizosaccharomyces pombe*.

5. The recombinant *Methylococcus capsulatus* bacterium of claim 1, wherein the one or more exogenous nucleic acids or genes encode enzymes comprising SEQ ID NO.: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 or SEQ ID NO: 22.

6. A process for producing succinic acid from a carbon source using the recombinant *Methylococcus capsulatus* bacterium of claim 1, said process comprising:
receiving at least one carbon source selected from the group consisting of biogas and methane as input;
culturing the bacterium in the input, thereby converting the input into succinic acid; and
optionally, purifying or separating the succinic produced from the culture for obtaining the succinic acid.

7. The process as claimed in claim 6, wherein the input carbon source has a ratio of methane to carbon dioxide ranging from about 95:5 to about 50:50.

8. The process of claim 6, wherein the temperature maintained throughout the conversion of the input to succinic acid is in the range of about 35° C. to 50° C., and wherein the pH maintained throughout the conversion of the input to succinic acid is in the range of about 3 to about 7.

9. A process for producing succinic acid from organic waste using the recombinant *Methylococcus capsulatus* bacterium of claim 1, said process comprising:
receiving organic waste as input;
anaerobic ally digesting the organic waste to biogas;
culturing the bacterium in the biogas so generated thereby converting the biogas to succinic acid while maintaining:
the temperature in the range of about 35° C. to 50° C.,
the pH in the range of about 4 to about 7, and
the dissolved oxygen concentration at less than 20%; and
optionally, purifying the succinic acid produced from the culture for obtaining the succinic acid.

10. The process as claimed in claim 9, wherein the biogas produced by anaerobically digesting the organic waste is optionally cleaned to remove carbon dioxide and other impurities present in the biogas to obtain methane for producing succinic acid from methane thereafter.

* * * * *